United States Patent
Wang et al.

(10) Patent No.: US 10,792,331 B2
(45) Date of Patent: Oct. 6, 2020

(54) METHODS FOR REDUCING CARDIOTOXICITY FROM CHEMOTHERAPY BY ADMINISTERING HUMANIN ANALOG COMPOSITIONS

(71) Applicant: LOS ANGELES BIOMEDICAL RESEARCH INSTITUTE AT HARBOR-UCLA MEDICAL CENTER, Torrance, CA (US)

(72) Inventors: Christina Wang, Long Beach, CA (US); YanHe Lue, Torrance, CA (US); Ronald S. Swerdloff, Long Beach, CA (US)

(73) Assignee: LOS ANGELES BIOMEDICAL RESEARCH INSTITUTE AT HARBOR-UCLA MEDICAL CENTER, Torrance, CA (US)

( * ) Notice: Subject to any disclaimer, the term of this patent is extended or adjusted under 35 U.S.C. 154(b) by 0 days.

(21) Appl. No.: 15/916,204

(22) Filed: Mar. 8, 2018

(65) Prior Publication Data
US 2018/0353570 A1    Dec. 13, 2018

Related U.S. Application Data

(63) Continuation-in-part of application No. PCT/US2016/050780, filed on Sep. 8, 2016.

(60) Provisional application No. 62/629,911, filed on Feb. 13, 2018, provisional application No. 62/215,974, filed on Sep. 9, 2015.

(51) Int. Cl.
*A61K 38/17*    (2006.01)
*A61P 9/00*    (2006.01)
*A61K 31/496*    (2006.01)

(52) U.S. Cl.
CPC ............ *A61K 38/1709* (2013.01); *A61P 9/00* (2018.01); *A61K 31/496* (2013.01); *A61K 2300/00* (2013.01)

(58) Field of Classification Search
None
See application file for complete search history.

(56) References Cited

U.S. PATENT DOCUMENTS

| | | | | |
|---|---|---|---|---|
| 5,817,321 | A | * 10/1998 | Alakhov | A61K 9/0019 424/400 |
| 2005/0020666 | A1 | * 1/2005 | Mukherjee | A61K 31/00 514/419 |
| 2012/0252722 | A1 | 10/2012 | Mascarenhas | |
| 2013/0053323 | A1 | 2/2013 | Eriksson et al. | |

FOREIGN PATENT DOCUMENTS

WO    2013074871 A2    5/2013

OTHER PUBLICATIONS

Cohen, Pinchas, New Role for the Mitochondrial Peptide Humanin: Protective Agent Against Chemotherapy-Induced Side Effects, JNCI J Natl Cancer Inst (first published online Mar. 1, 2014) vol. 106, No. 3, pp. 1-2.
Muzumdar et al., Acute Humanin Therapy Attenuates Myocardial Ischemia and Reperfusion Injury in Mice. Arteriosclerosis, Thrombosis, and Vascular Biology (Sep. 15, 2010) vol. 30, pp. 1940-1948.
Hashimoto et al., A rescue factor abolishing neuronal cell death by a wide spectrum of familial Alzheimer's disease genes and Abeta. PNAS (May 22, 2001) vol. 98 No. 11, pp. 6336-6341.
Patent Cooperation Treaty, International Search Report for PCT/US2016/050780, dated Dec. 7, 2016, pp. 1-4.

* cited by examiner

*Primary Examiner* — Elly-Gerald Stoica
(74) *Attorney, Agent, or Firm* — Pillsbury Winthrop Shaw Pittman LLP

(57) ABSTRACT

Provided herein are compositions, methods and uses of humanin or a humanin analog, for example, in treating a subject with humanin or a humanin analog, in part, to reduce, decrease, or inhibit cardiotoxicity caused or induced by an anti-cancer or anti-tumor therapeutic agent, or to protect or preserve cardiac function in the presence of an anti-tumor or anti-cancer therapeutic agent. In some aspects, humanin or humanin analogs, alone or in combination with another cardioprotective agent such as Dexrazoxane are used in combination with a chemotherapeutic agent to treat a hyperproliferative disease or disorder.

26 Claims, 17 Drawing Sheets
(7 of 17 Drawing Sheet(s) Filed in Color)
Specification includes a Sequence Listing.

| Group Total N=45 | Shave and rose wax Day -2 | Inoculation Day 0 | Wt. measure/hair picture Days 0,3,6,9,12,15,18,21, 24,27,30,33,36,39 | Tumor Volume Measure Days 9,12,15,18,21,24,27,30,33,36,39 | Dox IP Days 2,9,16,23, 30,37 (6 doses) | HNG IP Daily, Days 2-40 (25-39 doses) | Echo Days 26/40 | Sacrifice Day 27 or 41 |
|---|---|---|---|---|---|---|---|---|
| Control n=6 | + | - | + | - | - | - | + | + |
| Untreated N=10 | + | + | + | + | - | - | +(D26) | +(D27) |
| HNG N=10 | + | + | + | + | - | + | +(D26) | +(D27) |
| Dox N=10 | + | + | + | + | + | | +(D40) | +(D41) |
| Dox+HNG N=10 | + | + | + | + | + | + | +(D40) | +(D41) |

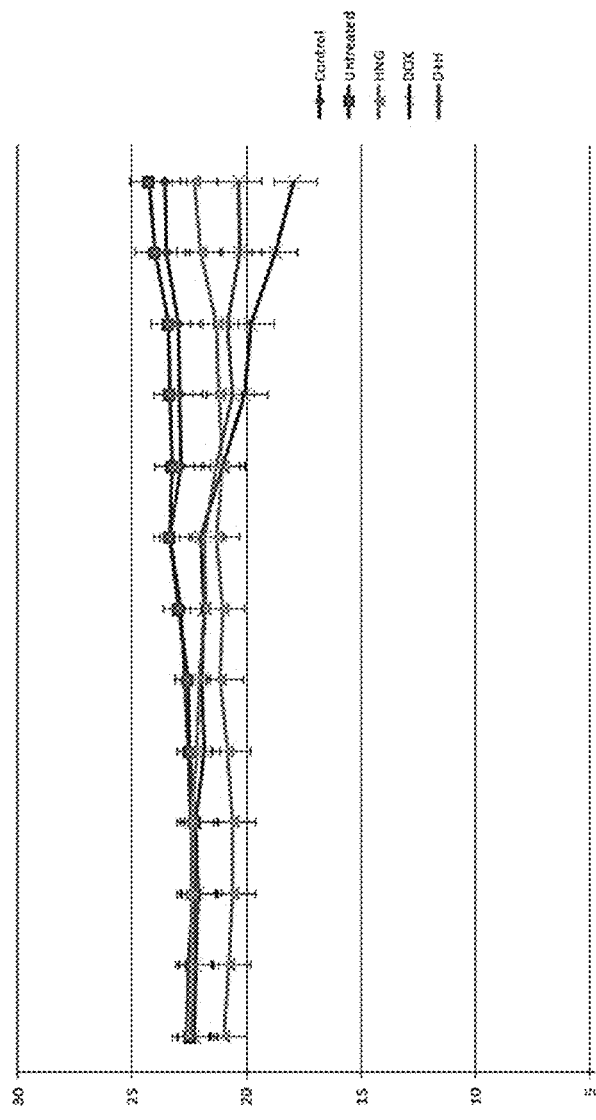
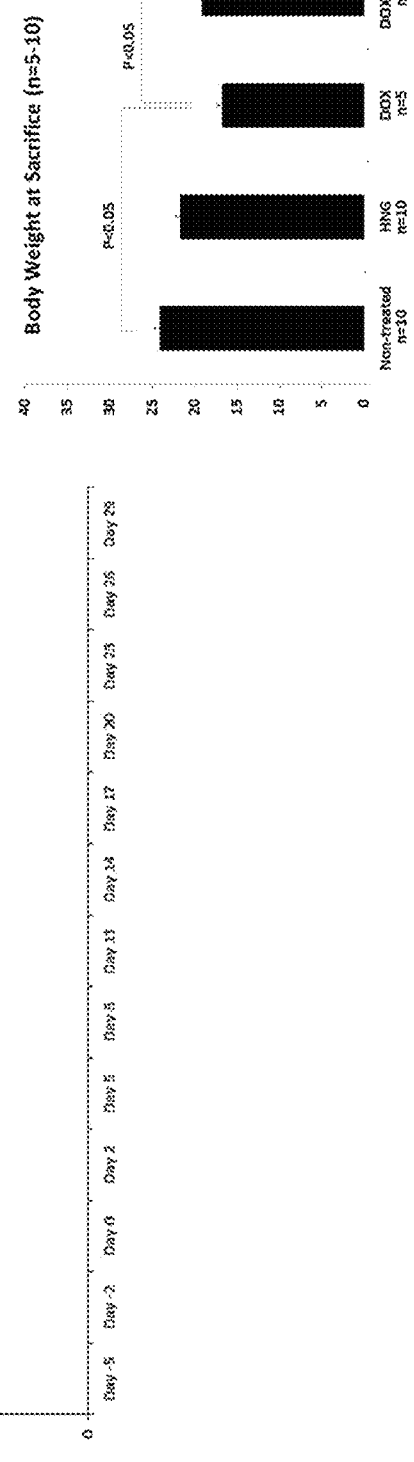
Fig. 2A
Fig. 2B

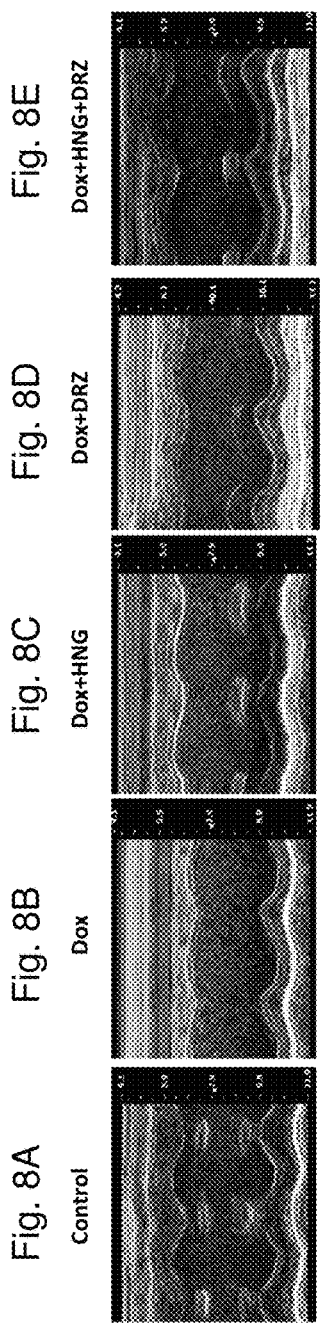
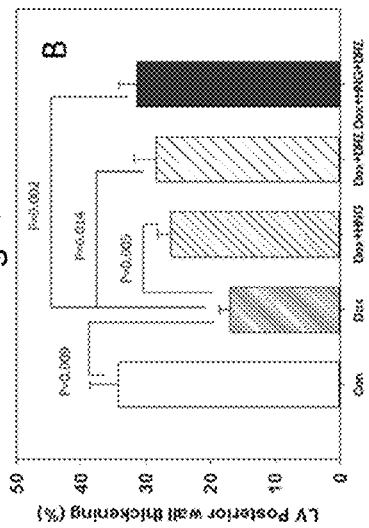
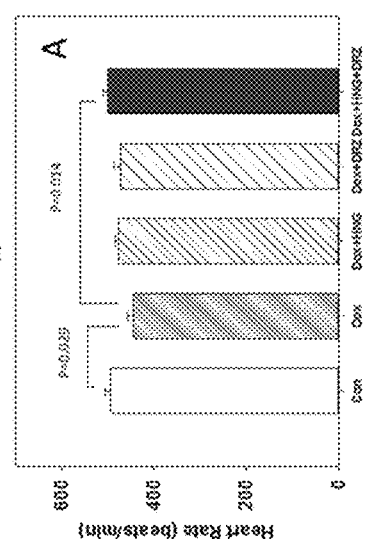
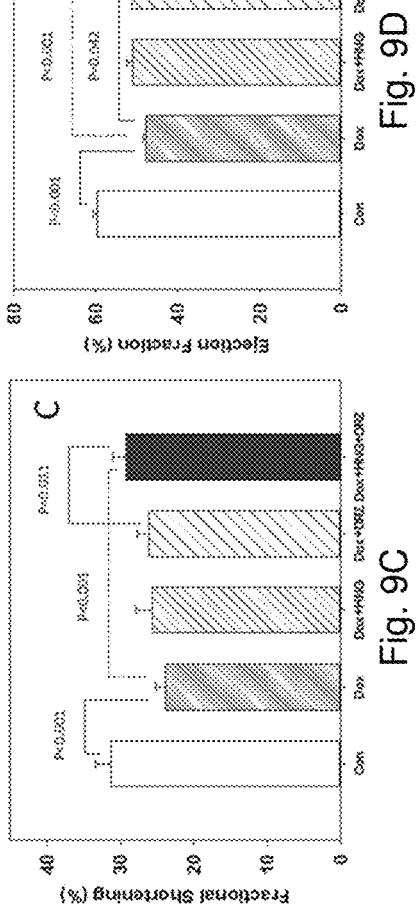

ANF Levels

Fibrosis Area

METHODS FOR REDUCING CARDIOTOXICITY FROM CHEMOTHERAPY BY ADMINISTERING HUMANIN ANALOG COMPOSITIONS

RELATED APPLICATIONS

This application is a continuation-in-part of International Application No. PCT/US2016/050780, filed Sep. 8, 2016, which claims priority to U.S. Provisional Patent Application No. 62/215,974, filed Sep. 9, 2015 and claims priority to U.S. Provisional Patent Application No. 62/629,911 filed Feb. 13, 2018. The subject matter of each of these applications are incorporated herein by reference in their entirety.

BACKGROUND

Therapy for cancer has progressed dramatically reducing the morbidity and mortality of many cancers. Current concept suggests that cancer is a manageable chronic disease. Thus it is important to limit comorbidities arising from anticancer therapy for cancer survivors.

Cardiotoxicity occurs with cancer chemo- and targeted-therapy. The severity depends on the type of agent, the route of administration, acute/immediate or chronic related to cumulative dose, and underlying cardiac disease of the patient (Yeh, 2006; Yeh, et al., 2004). Anthracylines (Doxorubicin [DOX], Daunorubicin, Epirubicin, Idarubicin) are the class of chemotherapeutic agents that has established cardiotoxicity. Acute cardiotoxicity manifests as ST segment changes and T wave abnormalities, whereas chronic toxicity is dose related and presents as congestive heart failure and left ventricular dysfunction. The incidence of congestive heart failure in DOX treated patients with cancer is 3 to 5% at a cumulative dose of 400 mg/m$^2$ and 7 to 26% at a cumulative dose of 550 mg/m$^2$ (Guo & Wong, 2014). The mechanism of action may be due to generation of iron-related reactive oxygen species and binding to topoisomerase 2β to induce mitochondrial dysfunction (Berthiaume & Wallace, 2007; Gammella, et al., 2014; Wallace, 2003). Doses of DOX>550 mg/m$^2$ cause increased rates of cardiotoxicity and cardiomyopathy. The late cardiotoxicity causes increased morbidity and mortality in cancer survivor.

Humanin (HN), a 24-amino acid mitochondrial derived peptide, is an endogenous anti-apoptotic peptide in many tissues. HN is expressed in germ cells and Leydig cells in testes (Colon, et al., 2006; Moretti, et al., 2010). HN reportedly protects against male germ cell apoptosis induced by testicular hormonal deprivation (Jia, et al., 2013; Lue, et al., 2010). In addition to the finding of endogenous HN (peptide or gene) in normal tissues and cells, HN has been proposed as an potential oncopeptide (Maximov, et al., 2002) because HN gene is expressed in cutaneous T-cell lymphoma (Hartmann, et al., 2008), diffuse large B-cell lymphoma (Tarantul & Hunsmann, 2001), and gastric cancer (Mottaghi-Dastjerdi, et al., 2014).

SUMMARY

In some aspects presented herein is a method of reducing, decreasing, or inhibiting cardiotoxicity in a subject from an anti-cancer or anti-tumor therapeutic agent suppression or death, where cardiotoxicity is induced, promoted, increased, or stimulated by the anti-cancer or anti-tumor therapy comprising administering to a subject prior to, during or after treatment with an anti-cancer or anti-tumor therapeutic agent an amount of humanin or a humanin analog sufficient to protect, reduce, decrease, or inhibit cardiotoxicity induced, promoted, increased, or stimulated by the anti-cancer or anti-tumor therapeutic agent.

Also presented herein in certain aspects is a method of protecting or preserving cardiac function in a subject administered an anti-cancer or anti-tumor therapeutic agent, wherein cardiac function may be impaired by an anti-cancer or anti-tumor therapeutic agent. In one embodiment, a method includes administering to a subject prior to, during or after treatment with the anti-cancer or anti-tumor therapeutic agent an amount of humanin or a humanin analog sufficient to protect or preserve cardiac function in the subject.

Also presented herein in some aspects is a humanin or a humanin analog in the manufacture of a medicament 1) for reducing, decreasing, or inhibiting cardiotoxicity from a anticancer or anti-tumor therapeutic agent, or 2) for protecting or preserving cardiac function in presence of an anti-cancer or anti-tumor therapeutic agent, e.g., in a subject administered an anticancer or anti-tumor therapeutic agent.

In certain aspects of the methods and uses the anti-cancer or anti-tumor therapeutic agent comprises an alkylating agent, an anthracycline, an anti-metabolite, plant extract, plant alkaloid, nitrosourea, hormone, nucleoside or nucleotide analog. In some aspects of the method or use the anti-cancer or anti-tumor therapeutic agent comprises a DNA intercalating agent or an agent that attaches or bonds to DNA.

In more particular aspects of the methods and uses the anti-cancer or anti-tumor therapeutic agent comprises Doxorubicin, Epirubicin, Idarubicin, Daunorubicin, Valrubicin, Mitoxantrone, Paclitaxel, Cisplatin, Carboplatin, Oxiplatin, Trastuzumab, Bevacizumab, Lapatinib, Alemtuzumab or Imatinib. In some aspects the anti-cancer or anti-tumor therapeutic agent is not Daunorubicin.

In certain embodiments, a further cardioprotective agent is administered in combination with humanin or a humanin analog to reduce, inhibit or decrease cardiotoxicity. In some aspects, the cardioprotective agent comprises Dexrazoxane.

In some aspects the humanin or a humanin analog does not substantially reduce, decrease, suppress or inhibit efficacy or activity of the anti-cancer or anti-tumor therapeutic agent. In some embodiments of the methods and uses the efficacy or activity of the anti-cancer or anti-tumor therapeutic agent comprises partial or complete destruction of a hyperproliferating cell, or a neoplastic, tumor, cancer or malignant cell mass, volume, size or numbers of cells; stimulating, inducing or increasing hyperproliferating cell or neoplastic, tumor, cancer or malignant cell necrosis, lysis or apoptosis; reduces hyperproliferating cell or neoplasia, tumor, cancer or malignancy volume size or cell mass; inhibits or prevents progression or an increase in hyperproliferating cell or neoplasia, tumor, cancer or malignancy volume, mass, size or cell numbers, reduces neoplasia, tumor, cancer or malignancy metastasis volume, size or cell mass; or prolongs lifespan.

In some embodiments, a method or use reduces, decreases, or inhibits damage to cardiac cells or cardiac tissue. In some embodiments, a method or use reduces, decreases, or inhibits cardiac mortality of a subject. In some embodiments, a method or use reduces, decreases, or inhibits impairment of cardiac function caused or induced by the anti-cancer or anti-tumor therapeutic agent. In some embodiments, a method or use decreases, or inhibits impairment of cardiac function, for example, as determined by electrocardiogram, magnetic resonance imaging (MRI) or computerized tomography (CT) scan. In some embodiments, cardiac function impairment comprises decrease in ejection fraction and/or fractional ventricular shortening. In some embodiments, a method or use restores, stabilizes or inhibits or prevents a reduction or decrease in ejection fraction and/or fractional ventricular shortening caused or induced by the anti-cancer or anti-tumor therapeutic agent.

In certain embodiments humanin comprises the sequence: MAPRGFSCLLLLTSEIDLPVKRRA (SEQ ID NO:1). In certain embodiments humanin analog comprises the sequence: MAPRGFSCLLLLTGEIDLPVKRRA (HN-S14G; SEQ ID NO:2), or any sequence set forth in Tables 1-4.

In some embodiments, the neoplasia, tumor, cancer or malignancy is metastatic, non-metastatic or benign. In some embodiments, the neoplasia, tumor, cancer or malignancy comprises a solid cellular mass. In some embodiments, the neoplasia, tumor, cancer or malignancy comprises hematopoietic cells. In certain embodiments, the neoplasia, tumor, cancer or malignancy comprises a carcinoma, sarcoma, lymphoma, leukemia, adenoma, adenocarcinoma, melanoma, glioma, glioblastoma, meningioma, neuroblastoma, retinoblastoma, astrocytoma, oligodendrocytoma, mesothelioma, reticuloendothelial, lymphatic or haematopoietic neoplasia, tumor, cancer or malignancy. In some embodiments, the sarcoma comprises a lymphosarcoma, liposarcoma, osteosarcoma, chondrosarcoma, leiomyosarcoma, rhabdomyosarcoma or fibrosarcoma. In some embodiments, the haematopoietic cell neoplasia, tumor, cancer or malignancy comprises a myeloma, lymphoma or leukemia. In some embodiments, the neoplasia, tumor, cancer or malignancy comprises a metastatic melanoma. In some aspects of the methods and uses the neoplasia, tumor, cancer or malignancy comprises a lung, thyroid, head or neck, nasopharynx, throat, nose or sinuses, brain, spine, breast, adrenal gland, pituitary gland, thyroid, lymph, gastrointestinal (mouth, esophagus, stomach, duodenum, ileum, jejunum (small intestine), colon, rectum), genitourinary tract (uterus, ovary, cervix, endometrial, bladder, testicle, penis, prostate), kidney, pancreas, liver, bone, bone marrow, lymph, blood, muscle, or skin, lung, biliary tract, or hematologic neoplasia, tumor, or cancer.

In some embodiments the methods or uses further comprise administration or use of a second, third or fourth anti-cancer or anti-tumor therapeutic agent. In some embodiments the humanin or humanin analog, with or without another cardioprotective agent (e.g., DRZ) is administered or used prior to, substantially contemporaneously with or following administration of the anti-cancer or anti-tumor therapeutic agent. In some embodiments the humanin or humanin analog is administered or used in combination with the anti-cancer or anti-tumor therapeutic agent. In some embodiments the humanin or humanin analog is administered or used in one or more dose amounts of 0.05 to 50 mg/Kg per day. In some embodiments humanin or the humanin analog is administered or used in one or more dose amounts of 0.1 to 25 mg/Kg per day, 0.5 to 15 mg/Kg per day, or 1.0 to 10 mg/Kg per day.

In some aspects of the methods and uses a subject has a hyperproliferative disease or disorder. In some aspects of the methods and uses the subject has a metastatic or non-metastatic neoplasia, tumor, cancer or malignancy.

In some embodiments of the methods and uses the subject has undergone surgical resection, chemotherapy, immunotherapy, ionizing or chemical radiotherapy, local or regional thermal (hyperthermia) therapy, or vaccination. In some embodiments the subject is or is not a candidate for surgical resection, chemotherapy, immunotherapy, ionizing or chemical radiotherapy, local or regional thermal (hyperthermia) therapy, or vaccination. In some embodiments the subject is a mammal. In some embodiments the subject is a primate. In some embodiments the subject is a human.

Certain aspects of the technology are described further in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments. The patent or application file contains at least one drawing executed in color. Copies of this patent or patent application publication with color drawing(s) will be provided by the Office upon request and payment of the necessary fee.

FIG. 2A shows body weights (grams, y-axis) of control, untreated, HNG, DOX and HNG+DOX treated mice. Control, untreated, and HNG treated mice increased weight, whereas DOX and HNG+DOX treated mice decreased weight with DOX losing significantly more weight (see inset). FIG. 2B shows a graphical summary of the data shown in FIG. 2A. Body weight is shown on the y-axis (grams).

FIGS. 8A-E show representative M-mode echocardiogra Photo images of mouse hearts from five different treatment groups as indicated at the top of each image. FIG. 8A represents Control, FIG. 8B represents Dox, FIG. 8C represents Dox+HNG, FIG. 8D represents Dox+DRZ, and FIG. 8E represents Dox+HNG+DRZ.

FIGS. 9A-9D show a bar graph for the five treatment groups (i.e., Control, Dox, Dox+HNG, Dox+DRZ and Dox+HNG+DRZ) as indicated at the bottom of each graph. FIG. 9A shows heart rate, FIG. 9B shows left ventricle posterior wall thickening, FIG. 9C shows fractional shortening, and FIG. 9D shows ejection fraction.

FIG. 11C shows a graph of Apoptotic Index (Tunel-positive myocyte nuclei/1000 myocyte nuclei; y-axis) in Control, Dox, Dox+HNG, Dox+DRZ and Dox+HNG+DRZ treated mouse hearts as indicated on the x-axis.

FIG. 14A shows Western blot images detecting the presence of UPC2. FIG. 14B shows a bar graph quantitating the relative chemoluminance signals of UPC2 expression shown in the top panel. HNG, DRZ or HNG+DRZ significantly normalized Ucp2 protein suppressed by Dox to control levels.

DETAILED DESCRIPTION

Figures 1A, 1B:
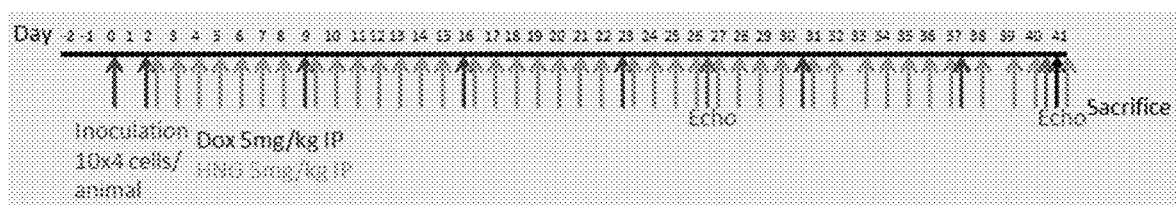
FIG. 1A shows the schedule of administration for mice treated with HNG, DOX or HNG+Dox.
FIG. 1B shows a summary of the activities and data collection that took place. Plasma: BNP, smear, CBC, flow cytometry, IGF-1, IGF-BP3 if serum sample left. Tumor: Measure tumor weight, half tumor and surrounding tissue for histology, half snap frozen. Heart: weight. GI: ileum (3 cm above cecum), fix for histology. Liver: weight, half for histology, half snap frozen. Spleen: weight, half for histology, half snap frozen. Lung: look for metastasis, if yes, take pictures and fix for histology. Bone Marrow: fix. Brain: fix. Testis: weight, one for histology, one for snap frozen. Epididymis: sperm count.

Humanin (HN), a 24-amino acid mitochondrial derived peptide, is an endogenous anti-apoptotic peptide in many tissues. As disclosed herein, HN and HN analogs can be used as agents to reduce, decrease, or inhibit cardiotoxicity caused or induced by an anti-cancer or anti-tumor therapeutic agent, and/or protect or preserve cardiac function in the presence of an anti-cancer or anti-tumor therapeutic agent. For example, HN and HN analogs were able to protect animals against chemotherapy induced cardiac impairment and limit/protect cardiac cytotoxicity/damage caused by chemotherapy (doxorubicin (Dox)) treatment. These discoveries are clinically relevant, as methods, uses and compositions described herein can be used as an adjunct to treatments of hyperproliferative diseases and disorders, (e.g., neoplasias, tumors, cancers and malignancies) in which cardiac function is impaired or cardiac cells are suppressed or killed by treatment with chemotherapy. In certain embodiments, method and compositions herein can protect cancer patient from cardiac adverse acute chemotherapy effects. For example, method and compositions herein can protect or preserve a subject from treatment-induced cardiac function impairment and/or cardiotoxicity, which can lead to damage to cardiac cells or cardiac tissue and/or increase the risk of cardiac mortality.

In some embodiments, humanin or a humanin analog is administered to a subject in combination with another cardioprotective agent. Any suitable cardioprotective agent can be used in combination with humanin or a humanin analog as per the methods and uses described herein. In certain embodiments, a cardioprotective agent comprises Dexrazoxane (DRZ) or a salt of Dexrazoxane, e.g., a pharmaceutically acceptable salt of Dexrazoxane. In some embodiments, a cardioprotective agent comprises Dexrazoxane hydrochloride. In some embodiments, Dexazoxane is ZINECARD® or CARDIOXANE®.

Humanin and humanin analogues such as HNG, when used or administered alone, or in combination with another cardioprotective agent, can provide enhanced cardioprotective effects from chemotherapeutic agents. Accordingly, in certain embodiments, composition and methods presented herein can protect a cancer patient from adverse acute chemotherapy effects on cardiac tissues. In some embodiments, methods presented herein comprise administering humanin or a humanin analogue, optionally in combination with another cardioprotective agent (e.g., DRZ), to a cancer patient undergoing chemotherapy.

Methods, uses and compositions herein are applicable to any subject. A subject is any living or non-living organism, including but not limited to a mammal such as a human. A subject can also be a non-human animal, non-limiting examples of which include a reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), primate (e.g., monkey, ape, chimpanzee), ursid (e.g., bear), bird (e.g., poultry, fowl), dog, cat, mouse, rat, fish, dolphin, whale and shark. A subject may be any age (e.g., an embryo, a fetus, infant, child, adult). A subject can be of any sex (e.g., male, female, or combination thereof). A subject may be pregnant. In particular embodiments a subject is a human.

In some embodiments a subject is a human patient. A patient can be any subject suspected of having, diagnosed with, or undergoing treatment for an ailment, disease or infection, or a subject who could benefit from a use or method herein. For example, in certain embodiments a patient is a subject diagnosed with a hyperproliferative disorder or disease, such as cancer and/or undergoing a treatment for a cancer.

Cardiac cells which may benefit from a treatment or use include any cell of the heart that contributes to the structure, function (mechanical/electrical) of the heart. Particular examples include cardiomyocytes (atrial and ventricular) which form the myocardium and cardiac fibroblasts. Additional cardiac cells include endothelial cells. Specialized cardiac cells include Pacemaker cells and Purkinje fibers in the conduction system that generate and conduct electrical impulses. The sinoatrial node (SAN), which is composed of pacemaker cells, resides in the right atrium generating impulses to initiate heart contraction. The atrioventricular node (AVN), located between the atria and ventricles, conducts an electrical impulse from the atria to the ventricles. Accordingly, cardiac damage or cardiac impairment may occur due to toxicity towards any one of such cells, or a combination thereof. As such, protection and/or preservation in accordance with the methods and uses herein may be directed towards any one of such cells, or a combination thereof.

In some embodiments, suppression and grammatical variations thereof mean an adverse effect of an anti-cancer or anti-tumor therapeutic agent on cardiac cells, tissue or cardiac function that results in the inhibition, reduction or loss of one or more functions of the heart, e.g., cardiac impairment. In some embodiments the inhibition, reduction or loss of one or more cell functions refers to the loss of, or inhibition of, a cell's ability to replicate (e.g., proliferate) and/or undergo mitosis or meiosis. In some embodiments the inhibition, reduction or loss of one or more cell functions refers to the loss of, or inhibition of, a cell's ability to metabolize oxygen, proteins, fatty acids, carbohydrates and/or glucose. In some embodiments the inhibition, reduction or loss of one or more cell functions refers to the loss of, or inhibition of, a cell's ability to initiate, or maintain contraction function or activity. In some embodiments the inhibition, reduction or loss of one or more cell functions refers to the loss of, or inhibition of, a cell's ability to initiate or respond to an electrical signal.

In some embodiments, an anti-cancer or anti-tumor therapeutic agent causes, promotes, increases or induces cell death or apoptosis of a cardiac cell. Cell death can be any type of cell death that is induced by any known or unknown mechanism. In some embodiments cell death refers to apoptotic death (e.g., apoptosis), autophagic cell death (autophagy) and/or necrotic cell death (e.g., necrosis). In some embodiments cell death refers to a loss of cell viability. Cell death and/or viability can be determined by a suitable assay known in the art or described herein. Non-limiting examples include cardiac function, contractile function or electrical signal responsiveness. Additional assays include membrane alteration assays (e.g., as measured by annexin-V binding, uptake of impermeable dyes such as propidium iodide, trypan blue, LDH release, the like or combinations thereof), caspase activation assays (e.g., as measured by peptide substrate cleavage, substrate cleavage (e.g., PARP, M30), caspase processing, the like or combinations thereof), DNA fragmentation assays (e.g., TUNEL assay, or assessment of DNA laddering, cytoplasmic nucleosomes, hypodiploid DNA, and release of incorporated nucleotides (e.g., BrdU), the like, or combinations thereof), mitochondrial damage assays (e.g., measurements of cytochrome C release, mitochondrial membrane potential, ATP production, electron transport activity (e.g., WST-1 or MTI assays)), the like or combinations thereof.

Cardiac cytotoxicity, impairment of cardiac function and/or impairment or death of cardiac cells can be induced by an anti-cancer or anti-tumor therapeutic agent. Cardiac cytotoxicity, impairment of cardiac function and/or impairment or death of cardiac cells can be induced when a cardiac cell comes into contact with one or more anti-cancer or anti-tumor therapeutic agents. In some embodiments an anti-cancer or anti-tumor therapeutic agent is cytotoxic to a cardiac cell. In certain embodiments, administration of an anti-cancer or anti-tumor therapeutic agent to a subject induces, causes, promotes, increases and/or stimulates cardiac cytotoxicity, impairment of cardiac function and/or impairment or death of cardiac cells. Cardiac cytotoxicity, impairment of cardiac function and/or impairment or death of cardiac cells can occur or is worse in the absence of a method described herein (e.g., in the absence of administering humanin or a humanin analog, or another cardioprotective agent, such as DRZ).

In certain embodiments, administration of an anti-cancer or anti-tumor therapeutic agent to a subject reduces, decreases, or inhibits maturation, proliferation and/or survival of cardiac cells in the absence of a method described herein (e.g., in the absence of administering humanin or a humanin analog). In certain embodiments, administration of an anti-cancer or anti-tumor therapeutic agent to a subject damages cardiac cells or cardiac function in the absence of a method described herein (e.g., in the absence of administering humanin or a humanin analog). Cell damage may include damage to genomic DNA, mitochondria or other organelles, mitochondrial DNA, mitochondrial cell walls or phospholipid membranes.

Anti-cancer or anti-tumor therapeutic agents can include a variety of poisons, venoms, toxins, proteins, antibodies and inhibitors that can cause, promote or induce impairment of cardiac function and/or death of a cardiac cells by a variety of mechanisms. In some embodiments a therapeutic agent comprises a cytotoxic compound. Cytotoxic compound can induce cell death of cardiac cells, damage cardiac cells and/or inhibit one or more functions of cardiac cells. Cytotoxic compounds can be organic compounds. In some embodiments cytotoxic compounds are small organic compounds with a molecular weight between 1 and about 5000 Daltons, 1 and about 2500 Daltons, 1 and about 1000 Daltons, 1 and about 500 Daltons or between about 50 and about 1000 Daltons.

Anti-cancer or anti-tumor therapeutic agents can be monoclonal or polyclonal antibodies. Anti-cancer or anti-tumor therapeutic agents can be polypeptides or fusion proteins. In some embodiments, Anti-cancer or anti-tumor therapeutic agents are not cytotoxic until after they are administered to a subject wherein the therapeutic agents are metabolized into a cytotoxic compound. In some embodiments a cardiac cell is contacted with an anti-cancer or anti-tumor therapeutic agent and the cardiac cell metabolizes the therapeutic agent into a cytotoxic compound. Cardiac blood cells can be contacted directly or indirectly (e.g., by a targeted approach) with an anti-cancer or anti-tumor therapeutic agents agent.

Anti-cancer and/or anti-tumor therapeutic agents are often administered to a subject (e.g., a patient) for the treatment of a hyperproliferative disease or disorder. In some embodiments anti-cancer and/or anti-tumor therapeutic agents comprise or consist of one or more cytotoxic compounds. In some embodiments a therapeutic agent comprises a suitable chemotherapeutic agent. In some embodiments a therapeutic agent comprises or consists of an alkylating agent, an anthracycline, cytoskeletal disruptors, epothilones (e.g., epothilone), histone deacetylase inhibitors (e.g., vorinostat, romidepsin), inhibitors of topoisomerase I (e.g., irinotecan, topotecan), inhibitors of topoisomerase II (e.g., etoposide, teniposide, tafluposidean), kinase inhibitors, peptide antibiotics (e.g., bleomycin, actinomycin), platinum-based agents (e.g., carboplatin, cisplatin, oxaliplatin), retinoids (e.g., tretinoin, alitretinoin, bexarotene), vinca alkaloids and derivatives (e.g., vinblastine, vincristine, vindesine, vinorelbine), anti-metabolites, plant extracts, plant alkaloids, nitrosourea, hormone, nucleoside or nucleotide analog and combinations thereof. In some embodiments a therapeutic agent comprises a DNA intercalating agent or an agent that attaches to or bonds to DNA.

Non-limiting examples of alkylating agents include anthracyclines, which include doxorubicin, daunorubicin, epirubicin, idarubicin, mitoxantrone, valrubicin, known analogs and derivatives thereof. Non-limiting examples of cytoskeletal disruptors (e.g., taxanes) include paclitaxel, taxol, and docetaxel. Non-limiting examples of biologics include Trastuzumab, Bevacizumab, Lapatinib, Alemtuzumab and Imatinib, known analogs and derivatives thereof.

In some embodiments an anti-cancer or anti-tumor therapeutic agent (e.g., a chemotherapeutic agent, a cytotoxic compound) induces partial or complete destruction of some or all hyperproliferating cells in a subject. In some embodiments a therapeutic agent induces partial or complete destruction of a neoplastic, tumor, cancer or malignant cell mass in a subject. A therapeutic agent can decrease the volume or size of a neoplasia, neoplastic tumor, cancer or malignancy and/or reduce the numbers of hyperproliferating cells in a subject. In some embodiments a therapeutic agent stimulates and/or induces apoptosis, necrosis, and/or lysis of hyperproliferating cells or cells of a neoplastic tumor, cancer or malignant cell masses in a subject. In some embodiments a therapeutic agent inhibits or prevents progression of or an increase in hyperproliferating cells or a neoplasia, tumor, cancer or malignancy. In some embodiments a therapeutic agent prolongs lifespan of a subject comprising a hyperproliferating disease or disorder. The efficacy or activity of a therapeutic agent can be determined according to 1) its ability and effectiveness to induce partial or complete destruction of some or all hyperproliferating cells in a subject, 2) induce partial or complete destruction of a neoplastic, tumor, cancer or malignant cell mass in a subject, 3) decrease the volume or size of a neoplasia, neoplastic tumor, cancer or malignancy and/or reduce the numbers of hyperproliferating cells in a subject, 4) stimulate and/or induces apoptosis, necrosis, and/or lysis of hyperproliferating cells or cells of a neoplastic tumor, cancer or malignant cell masses in a subject, 5) inhibit or prevent progression of or an increase in hyperproliferating cells or a neoplasia, tumor, cancer or malignancy in a subject, and/or 6) prolong the lifespan of a subject comprising a hyperproliferating disease or disorder. In certain embodiments, the administration of humanin or a humanin analog does not substantially reduce, decrease, suppress or inhibit efficacy or activity of an anti-cancer or anti-tumor therapeutic agent.

In certain embodiments a method, use or composition herein protects or preserves cardiac function. In various embodiments, protection or preservation of cardiac function is from an anti-cancer or anti-tumor therapeutic agent.

In some embodiments compositions, uses and methods herein are used to treat subjects having, suspected of having, diagnosed with and/or being treated for a hyperproliferative disease or disorder. In some embodiments a hyperproliferative disease or disorder refers to a neoplasia, tumor, cancer or malignancy. In some embodiments a hyperproliferative disease or disorder refers to a subject having a neoplasia, tumor, cancer or malignancy. A hyperproliferative disease or disorder can be metastatic, non-metastatic or benign. In some embodiments a neoplasia, tumor, cancer or malignancy comprises a solid cellular mass.

In certain embodiments a malignant neoplasm comprises or consist of a fibrosarcoma, myxosarcoma, liposarcoma, chondrosarcoma, osteosarcoma, chordoma, malignant fibrous histiocytoma, hemangiosarcoma, angiosarcoma, lymphangiosarcoma, mesothelioma, leiomyosarcoma, rhabdomyosarcoma, squamous cell carcinoma, epidermoid carcinoma, malignant skin adnexal tumor, adenocarcinoma, hepatoma, hepatocellular carcinoma, renal cell carcinoma, hypernephroma, cholangiocarcinoma, transitional cell carcinoma, choriocarcinoma, seminoma, embryonal cell carcinoma, glioma, glioblastoma multiforme, neuroblastoma, medulloblastoma, malignant meningioma, malignant schwannoma, neurofibrosarcoma, parathyroid carcinoma, medullary carcinoma of thyroid, bronchial carcinoid, oat cell carcinoma, malignant pheochromocytoma, islet cell carcinoma, malignant carcinoid, retinoblastoma, chemodectoma, paraganglioma, malignant carcinoid, malignant paraganglioma, melanoma, malignant schwannoma, merkel cell neoplasm, cystosarcoma phylloides, wilms tumor, malignant ovarian tumors, malignant testicular tumors, the like, or combinations thereof. In certain embodiments a neoplasia, tumor, cancer or malignancy comprises a carcinoma, sarcoma, lymphoma, leukemia, adenoma, adenocarcinoma, melanoma, glioma, glioblastoma, Kaposi sarcoma, meningioma, neuroblastoma, retinoblastoma, astrocytoma, oligodendrocytoma, reticuloendothelial, lymphatic or haematopoietic neoplasia, tumor, cancer or malignancy. In certain embodiments a sarcoma comprises a lymphosarcoma, liposarcoma, osteosarcoma, chondrosarcoma, leiomyosarcoma, rhabdomyosarcoma or fibrosarcoma.

In some embodiments a hyperproliferative disease or disorder comprises hyperproliferative hematopoietic cells or a haematopoietic cell neoplasia. In some embodiments a haematopoietic cell neoplasia, tumor, cancer or malignancy comprises a myeloma, lymphoma or leukemia. In some embodiments a leukemia is an acute lymphocytic leukemia (ALL), acute myeloid leukemia (AML), chronic lymphocytic leukemia (CLL), chronic myeloid leukemia (CML), or chronic myelomonocytic leukemia (CMML). In certain embodiments a neoplasia, tumor, cancer or malignancy comprises a metastatic melanoma. In certain embodiments a neoplasia, tumor, cancer or malignancy comprises a lung, thyroid, head or neck, nasopharynx, throat, nose or sinuses, brain, spine, breast, adrenal gland, pituitary gland, thyroid, lymph, gastrointestinal (mouth, esophagus, stomach, duodenum, ileum, jejunum (small intestine), colon, rectum), genitourinary tract (uterus, ovary, cervix, endometrial, bladder, testicle, penis, prostate), kidney, pancreas, liver, bone, bone marrow, lymph, blood, muscle, or skin, lung, biliary tract, or hematologic neoplasia, tumor, or cancer.

In some embodiments methods, uses and compositions described herein are to treat a subject having undergone surgical resection, chemotherapy, immunotherapy, ionizing or chemical radiotherapy, local or regional thermal (hyperthermia) therapy, or vaccination. In some embodiments methods, uses and compositions described herein are not used to treat a subject having undergone surgical resection, chemotherapy, immunotherapy, ionizing or chemical radiotherapy, local or regional thermal (hyperthermia) therapy, or vaccination. In certain embodiments methods, uses and compositions described herein are not used to treat a subject that is a candidate for surgical resection, chemotherapy, immunotherapy, ionizing or chemical radiotherapy, local or regional thermal (hyperthermia) therapy, or vaccination.

In some embodiments a method, use or composition described herein protects cardiac cells in a subject from suppression and/or death. In some embodiments a method, use or composition described herein protects cardiac cells in a subject from an anti-cancer or anti-tumor therapeutic agent. Without being limited by theory, a method, use or composition described herein may protect cardiac cells by preserving viability and/or function from the deleterious effects (e.g., adverse effects) caused by administration of an anti-cancer or anti-tumor therapeutic agent. The term "protect" can mean to prevent, shelter, shield and/or insulate.

Without being limited by theory, a method, use or composition described herein may inhibit cardiac cell necrosis, autophagy or apoptosis induced by administration of a therapeutic agent (e.g., a cytotoxic compound). In certain embodiments a method, use or composition described herein may inhibit certain signaling pathways that may lead to apoptosis where the apoptotic pathway is activated by an anti-cancer or anti-tumor therapeutic agent. In certain embodiments a method, use or composition described herein may inhibit cardiac cell senescence.

In some embodiments a method, use or composition described herein reduces, decreases, or inhibits cardiotoxicity induced by a therapeutic agent by up to 100%, up to 50%, up to 30%, up to 20%, up to 15%, up to 10%, or up to 5%. In some embodiments a method or composition described herein reduces, decreases, or inhibits cardiac cell death caused, induced or promoted by an anti-cancer or anti-tumor therapeutic agent by at least 200%, at least 150%, at least 100%, at least 50%, at least 30%, at least 20%, at least 15%, at least 10%, or at least 5%. In certain embodiments a method, use or composition described herein decreases, reduces or inhibits impairment of cardiac function induced or promoted by an anti-cancer or anti-tumor therapeutic agent by at least 200%, at least 150%, at least 100%, at least 50%, at least 30%, at least 20%, at least 15%, at least 10%, or by at least 5%.

In some embodiments a method, use or composition described herein promotes and/or increases maturation, proliferation and/or survival of cardiac cells in a subject. In some embodiments a method, use or composition described herein promotes and/or increases maturation, proliferation and/or survival of cardiac cells in a subject administered an anti-cancer or anti-tumor therapeutic agent. In some embodiments administration or delivery of humanin or a humanin analog, alone or in combination with another cardioprotective agent (e.g., Dexrazoxane) promotes and/or increases maturation, proliferation and/or survival of cardiac cells in a subject administered an anti-cancer or anti-tumor therapeutic agent. In certain embodiments, administration of an anti-cancer or anti-tumor therapeutic agent to a subject reduces, decreases, or inhibits maturation, proliferation and/or survival of cardiac cells in the absence of administration or delivery of humanin or humanin analog, alone or in combination with another cardioprotective agent (e.g., Dexrazoxane), which reduction, decrease or inhibition can be completely or partially reversed by administration of humanin or a humanin analog. In some embodiments a method, use or composition described herein promote and/or increase maturation, proliferation and/or survival of cardiac cells by up to 200%, up to 100%, up to 50%, up to 30%, up to 20%, up to 15%, up to 10%, or up to 5%.

In some embodiments a method, use or composition described herein reduces, decreases, or inhibits cardiac mortality. In some embodiments a method, use or composition described herein protects or preserves cardiac function in the presence of an anti-cancer or anti-tumor therapeutic agent. In some embodiments a method, use or composition described herein reduces, decreases, or inhibits impairment of cardiac function as determined by an assay, such as an electrocardiogram, magnetic resonance imaging (MRI) or computerized tomography (CT) scan, in a subject that was administered or delivered an anti-cancer or anti-tumor therapeutic agent.

In certain embodiments, a composition or use thereof comprises humanin or a humanin analog. In certain embodiments, a composition or use thereof comprises humanin or a humanin analog and another cardioprotective agent such as Dexrazoxane. In certain embodiments, a method or use includes administering or delivering humanin or a humanin analog to a subject. In certain embodiments, a method or use includes administering or delivering humanin, or a humanin analog, and another cardioprotective agent (e.g., Dexrazoxane) to a subject. In certain embodiments, a method or use includes administering or delivering an effective amount of humanin or a humanin analog to a subject, optionally in combination with an effective amount of an anti-cancer or anti-tumor therapeutic agent. In certain embodiments, a method or use includes administering or delivering an effective amount of humanin or a humanin analog and another cardioprotective agent (e.g., Dexrazoxane) to a subject, optionally in combination with an effective amount of an anti-cancer or anti-tumor therapeutic agent. In certain embodiments, a method or use includes administering or delivering (i) humanin or a humanin analog, (ii) another cardioprotective agent (e.g., Dexrazoxane) and (iii) an anti-cancer or anti-tumor therapeutic agent to a subject.

Humanin or a humanin analog, optionally in combination with another cardioprotective agent (e.g., Dexrazoxane), can be administered or delivered to a subject prior to, during or after administration of an anti-cancer or anti-tumor therapeutic agent. Humanin or a humanin analog, optionally in combination with another cardioprotective agent (e.g., Dexrazoxane), can be administered to a subject prior to, during or after treatment with an anti-cancer or anti-tumor therapeutic agent. Humanin or a humanin analog, can be administered or delivered to a subject prior to, during or after administration of another cardioprotective agent (e.g., Dexrazoxane). In certain embodiments humanin or a humanin analog is administered or used prior to, substantially contemporaneously with or following administration of an anti-cancer or anti-tumor therapeutic agent. In certain embodiments humanin or a humanin analog, in combination with another cardioprotective agent (e.g., Dexrazoxane), is administered or used prior to, substantially contemporaneously with or following administration of an anti-cancer or anti-tumor therapeutic agent. In some embodiments humanin or a humanin analog, alone or in combination with another cardioprotective agent (e.g., Dexrazoxane), is administered or delivered to a subject prior to onset of cardiotoxicity.

In some embodiments, humanin comprises the amino acid sequence of SEQ ID NO: 1. A humanin analog can be a humanin variant. Exemplary non-limiting examples of humanin analogs and/or variants applicable to the methods, uses and compositions set forth herein are shown and described in Tables 1 to 4.

In some embodiments, administration or delivery of humanin or a humanin analog, alone or in combination with another cardioprotective agent (e.g., Dexrazoxane), reduces, decreases or inhibits damage to cardiac cells or cardiac tissue. In some embodiments humanin or a humanin analog, alone or in combination with another cardioprotective agent (e.g., Dexrazoxane), are administered or delivered in an amount sufficient to reduce, decrease, or inhibit cardiotoxicity caused by an anti-cancer or anti-tumor therapeutic agent. In some embodiments humanin or a humanin analog, alone or in combination with another cardioprotective agent (e.g., Dexrazoxane), are administered or delivered in an amount sufficient for protecting or preserving cardiac function in the presence of an anti-cancer or anti-tumor therapeutic agent. In some embodiments humanin or a humanin analog, alone or in combination with another cardioprotective agent (e.g., Dexrazoxane), are administered or delivered in an amount sufficient to reduce, decrease, or inhibit cardiac mortality in a subject (e.g., a subject treated with an anti-cancer or anti-tumor therapeutic agent). In some embodiments humanin or a humanin analog, alone or in combination with another cardioprotective agent (e.g., Dexrazoxane), are administered or delivered in an amount sufficient to reduce, decrease, or inhibit impairment of cardiac function in a subject (e.g., a subject treated with an anti-cancer or anti-tumor therapeutic agent). In particular aspects, humanin or a humanin analog, alone or in combination with another cardioprotective agent (e.g., Dexrazoxane), decreases, or inhibits impairment of cardiac function as determined by an electrocardiogram, magnetic resonance imaging (MRI) or computerized tomography (CT) scan; or reduces, decreases, or inhibits cardiac function impairment which comprises decrease in ejection fraction and/or fractional ventricular shortening. In further particular aspects, humanin or a humanin analog, alone or in combination with another cardioprotective agent (e.g., Dexrazoxane), restores, stabilizes, inhibits or prevents a reduction or decrease in ejection fraction and/or fractional ventricular shortening caused or induced by the anti-cancer or anti-tumor therapeutic agent. Methods of determining cardiotoxicity, damage to cardiac cells or cardiac tissue and impairment of cardiac function are known to the skilled artisan. Any suitable method can be used to determine, measure and/or assess cardiotoxicity, heart damage, damage to cardiac cells or cardiac tissue and impairment of cardiac function, non-limiting examples of which include chest X-rays, electrocardiogram (e.g., EKG or ECG), blood tests, physical examination (e.g., vitals, heart rate, blood pressure, etc.), exercise stress test, patient survey (e.g., to assess pain, angina, etc.), magnetic resonance imaging (MRI), computerized tomography (CT) scan, radionuclide ventriculography, multiple-gated acquisition scanning, cardiac catheterization, the like or combinations thereof. Accordingly, in certain embodiments, an amount of cardiotoxicity in a subject can readily be determined and/or measured. In some embodiments, a reduction, decrease, inhibition, increase, or stabilization of cardiotoxicity in a subject can be determined and/or measured using a suitable method by measuring and/or assessing an amount of cardiotoxicity before, after and/or during a treatment.

As disclosed herein, compositions, methods and uses of the invention, can be administered or delivered prior to, contemporaneously with or after an anti-cancer or anti-tumor therapeutic agent is administered or delivered, for example to a subject. Accordingly, methods, uses and compositions of the invention can be delivered prior to cardiotoxicity, damage to cardiac cells or cardiac tissue or impairment of cardiac function in order to protect or preserve cardiac cells.

"Prophylaxis" and grammatical variations thereof mean a method in which contact, administration or in vivo delivery to a subject is prior to administration or delivery of an anti-cancer or anti-tumor therapeutic agent, or prior to cardiotoxicity, damage to cardiac cells or cardiac tissue, or impairment of cardiac function. Administration or in vivo delivery to a subject can therefore be performed prior to onset or detection of cardiotoxicity. Accordingly, subjects are candidates for invention compositions, methods and uses, but the subject may not yet exhibit cardiotoxicity, damage to cardiac cells or cardiac tissue, or impairment of cardiac function.

Compositions, methods and uses, such as treatment methods and uses, can provide a detectable or measurable reduction, decrease, or inhibition of damage to cardiac cells or cardiac tissue, increase or stabilization of cardiac function, and/or reduce, decrease, or inhibit cardiac mortality of a subject. Compositions, methods and uses of the invention therefore include providing a therapeutic benefit or improvement to a subject, for example, as reflected by cardiac cell damage or heart function/impairment or mortality.

Compositions, methods and uses of the invention, can be administered or delivered in a sufficient or effective amount to a subject. An "effective amount" or "sufficient amount" refers to an amount that provides, in single or multiple doses, alone or in combination, with one or more other compositions (e.g., therapeutic agents or drugs), treatments, protocols, or therapeutic regimens, a detectable response of any duration of time (long or short term), an expected or desired outcome in or a benefit to a subject of any measurable or detectable degree or for any duration of time (e.g., for minutes, hours, days, months, years, or cured).

The doses for a "sufficient amount" for treatment (e.g., to provide a benefit or improvement) typically are effective to provide a response. In some embodiments a sufficient amount humanin or a humanin analog comprises an amount between about 0.01 to 100 mg/Kg (mg of humanin or a humanin analog per Kg of a subjects body weight) per day, between about 0.05 to 50 mg/Kg per day, between about 0.1 to 25 mg/Kg per day, between about 0.5 to 15 mg/Kg per day, between about 0.5 to 15 mg/Kg per day, or between about 1.0 to 10 mg/Kg per day. In some embodiments administering a sufficient amount of humanin or a humanin analog comprises administered one or more dose amounts of between about 0.01 to 100 mg/Kg per day, between about 0.05 to 50 mg/Kg per day, between about 0.1 to 25 mg/Kg per day, between about 0.5 to 15 mg/Kg per day, between about 0.5 to 15 mg/Kg per day, or between about 1.0 to 10 mg/Kg per day. A sufficient amount of humanin or a humanin analog may be administered in 1, 2, 3, 4, 5, 6, or 7 doses per day. In some embodiments a sufficient amount of humanin or a humanin analog is administered continuously or intermittently by a patch or suitable device (e.g., a pump). A sufficient amount of humanin or a humanin analog may be self-administered by a subject. For example a subject may use, in one or more doses, a sufficient amount of humanin or a humanin analog.

An effective amount or a sufficient amount can but need not be provided in a single administration, may require multiple administrations, and, can but need not be, administered alone or in combination with another composition (e.g., agent), treatment, protocol or therapeutic regimen. For example, the amount may be proportionally increased as the amount of an anti-cancer or anti-tumor therapeutic agent administered to the subject increases and the anticipated or predicted cardiotoxicity, damage to cardiac cells or cardiac tissue, cardiac impairment or cardiac mortality. Typically, as greater amounts of anti-cancer or anti-tumor therapeutic agent are administered the probability or occurrence of cardiotoxicity, damage to cardiac cells or cardiac tissue, cardiac impairment or cardiac mortality increases. The amount may also be determined by the need of the subject, type, status and severity of the cardiac damage that already exists (if any). In addition, an effective amount or a sufficient amount need not be effective or sufficient if given in single or multiple doses without a second composition (e.g., another drug or agent), treatment, protocol or therapeutic regimen, since additional doses, amounts or duration above and beyond such doses, or additional compositions (e.g., drugs or agents), treatments, protocols or therapeutic regimens may be included in order to be considered effective or sufficient in a given subject. Amounts considered effective also include amounts that result in a reduction of the use of another treatment, therapeutic regimen or protocol.

As is typical for treatment methods and uses, some subjects will exhibit a greater response, or less or no response to a given treatment method or use. An effective amount or a sufficient amount therefore need not be effective in each and every subject treated, prophylactically or therapeutically, nor a majority of treated subjects in a given group or population. An effective amount or a sufficient amount means effectiveness or sufficiency in a particular subject, not a group or the general population. Accordingly, appropriate amounts will depend upon the condition treated, the therapeutic effect desired, as well as the individual subject (e.g., the bioavailability within the subject, gender, age, etc.).

Effectiveness of a method or use, such as a method of treatment herein can provide a potential therapeutic benefit or improvement that can be ascertained by various methods. Such methods include, for example, measuring cardiac cell viability, damage to cardiac cells or cardiac tissue, heart function, and cardiac impairment. Measuring can be achieved by various means, including electrocardiogram, magnetic resonance imaging (MRI) or computerized tomography (CT) scan and/or cardiac function (e.g., stress) tests to ascertain effectiveness of a method, use or composition as set forth herein.

Humanin and/or humanin analogs, including in combination with another cardioprotective agent (e.g., Dexrazoxane), can be packaged in a suitable pharmaceutical formulation and/or dosage unit form for ease of administration and uniformity of dosage. "Dosage unit form" as used herein refers to physically discrete units suited as unitary dosages; each unit contains a quantity of the composition optionally in association with a carrier, excipient, diluent, or vehicle calculated to produce the desired treatment or therapeutic (e.g., beneficial) effect. The unit dosage forms can be varied according to factors including, but not necessarily limited to, the particular composition employed, the disorder or disease treated, the effect to be achieved, and the subject to be treated. Exemplary unit doses range from about 25-250, 250-500, 500-1,000, 1,000-2,500, 2,500-5,000, 5,000-25,000, or 5,000-50,000 pg; from about 50-500, 500-5,000, 5,000-25,000 or 25,000-50,000 ng; from about 50-500, 500-5,000, 5,000-25,000 or 25,000-50,000 µg; from about 25-250, 250-500, 500-1,000, 1,000-2,500, 2,500-5,000, 5,000-25,000, or 5,000-50,000 mg; and from about 1-5, 5-10, 10-25, 25-50, 50-100, 100-250, 250-500, 500-1,000, 1,000-2,500, or 2,500-5,000 grams.

As set forth herein, humanin and/or humanin analogs, alone or in combination with another cardioprotective agent (e.g., Dexrazoxane), and compositions thereof may be contacted or provided in vitro, ex vivo or administered or delivered in vivo to a subject or patient in various doses and amounts, and frequencies. For example, humanin or a humanin analog, alone or in combination with another cardioprotective agent (e.g., Dexrazoxane), or a composition thereof can be administered or delivered to provide the intended effect, as a single or as multiple dosages, for example, in an effective or sufficient amount.

Single or multiple (e.g., 2, 3, 4, 5, 6, 7, 8, 9, 10, or more times) administrations or doses can be administered on the same or consecutive days, alternating days or intermittently. For example, humanin or humanin analog, alone or in combination with another cardioprotective agent (e.g., Dexrazoxane), or a composition thereof can be administered one, two, three, four or more times daily, on alternating days, bi-weekly, weekly, monthly, bi-monthly, or annually. Humanin or humanin analog, alone or in combination with another cardioprotective agent (e.g., Dexrazoxane), or composition thereof can be administered for any appropriate duration, for example, for period of 1 hour, or less, e.g., 30 minutes or less, 15 minutes or less, 5 minutes or less, or 1 minute, or less.

Humanin or a humanin analog, alone or in combination with another cardioprotective agent (e.g., Dexrazoxane), or a composition thereof can be administered to a subject and methods and uses may be practiced prior to, substantially contemporaneously with, or within about 1-60 minutes, hours (e.g., within 1, 2, 3, 4, 5, 6, 8, 12, 24 hours), or days (1, 2, 3, 4, 5, 6, 7, 7-14, 14-21, 21-28, 28-45, 45-60, 60-90, etc.) of administration of an anti-cancer or anti-tumor therapeutic agent.

Humanin and/or a humanin analog, alone or in combination with another cardioprotective agent (e.g., Dexrazoxane), or a composition thereof can be administered or delivered via systemic, regional or local administration, and by any suitable route. For example, humanin and/or a humanin analog, alone or in combination with another cardioprotective agent (e.g., Dexrazoxane), or a composition thereof may be administered or delivered systemically, regionally or locally, via injection, infusion, orally (e.g., ingestion or inhalation), topically, intravenously, intra-arterially, intramuscularly, intraperitoneally, intradermally, subcutaneously, intracavity, intracranially, transdermally (topical), parenterally, e.g. transmucosally or intrarectally (enema) catheter, or optically. Humanin and/or a humanin analog, alone or in combination with another cardioprotective agent (e.g., Dexrazoxane), and compositions of the invention including pharmaceutical formulations may be administered via a (micro) encapsulated delivery system or packaged into an implant for administration.

Humanin or a humanin analog, alone or in combination with another cardioprotective agent (e.g., Dexrazoxane), or composition thereof can be incorporated into pharmaceutical compositions, e.g., a composition comprising a pharmaceutically acceptable carrier or excipient. Such pharmaceutical compositions are useful for, among other things, administration and delivery to a subject in vivo or ex vivo.

As used herein the terms "pharmaceutically acceptable" and "physiologically acceptable" mean a biologically acceptable formulation, gaseous, liquid or solid, or mixture thereof, which is suitable for one or more routes of administration, in vivo delivery or contact. A "pharmaceutically acceptable" or "physiologically acceptable" composition is a material that is not biologically or otherwise undesirable, e.g., the material may be administered to a subject without causing substantial undesirable biological effects. Thus, such a pharmaceutical composition may be used, for example in a formulation for administering or delivering humanin, a humanin analog, alone or in combination with another cardioprotective agent (e.g., Dexrazoxane), or compositions thereof to a subject.

Such compositions include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Pharmaceutical compositions can be formulated to be compatible with a particular route of administration or delivery, as set forth herein or known to one of skill in the art. Thus, pharmaceutical compositions include carriers, diluents, or excipients suitable for administration by various routes.

Compositions suitable for parenteral administration comprise aqueous and non-aqueous solutions, suspensions or emulsions of the active compound, which preparations are typically sterile and can be isotonic with the blood of the intended recipient. Non-limiting illustrative examples include water, saline, dextrose, fructose, ethanol, animal, vegetable or synthetic oils.

For transmucosal or transdermal administration (e.g., topical contact), penetrants can be included in the pharmaceutical composition. Penetrants are known in the art, and include, for example, for transmucosal administration, detergents, bile salts, and fusidic acid derivatives. For transdermal administration, the active ingredient can be formulated into aerosols, sprays, ointments, salves, gels, or creams as generally known in the art. For contact with skin, pharmaceutical compositions typically include ointments, creams, lotions, pastes, gels, sprays, aerosols, or oils. Carriers which may be used include petroleum jelly, lanolin, polyethylene glycols, alcohols, transdermal enhancers, and combinations thereof.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether, glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

Appropriate pharmaceutical compositions and delivery systems are known in the art (see, e.g., *Remington: The Science and Practice of Pharmacy* (2003) 20$^{th}$ ed., Mack Publishing Co., Easton, Pa.; *Remington's Pharmaceutical Sciences* (1990) 18$^{th}$ ed., Mack Publishing Co., Easton, Pa.; *The Merck Index* (1996) 12$^{th}$ ed., Merck Publishing Group, Whitehouse, N.J.; *Pharmaceutical Principles of Solid Dosage Forms* (1993), Technonic Publishing Co., Inc., Lancaster, Pa.; Ansel and Stoklosa, *Pharmaceutical Calculations* (2001) 11$^{th}$ ed., Lippincott Williams & Wilkins, Baltimore, Md.; and Poznansky et al., *Drug Delivery Systems* (1980), R. L. Juliano, ed., Oxford, N.Y., pp. 253-315).

The invention provides kits comprising humanin, humanin analogs, alone or in combination with another cardioprotective agent (e.g., Dexrazoxane), combination compositions and pharmaceutical formulations thereof, packaged into suitable packaging material. A kit optionally includes a label or packaging insert including a description of the components or instructions for use in vitro, in vivo, or ex vivo, of the components therein. Exemplary instructions include instructions for a method, treatment protocol or therapeutic regimen. The term "packaging material" refers to a physical structure housing the components of the kit. The packaging material can maintain the components sterilely, and can be made of material commonly used for such purposes (e.g., paper, corrugated fiber, glass, plastic, foil, ampules, vials, tubes, etc.).

Kits can include labels or inserts. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, optical disk such as CD- or DVD-ROM/RAM, DVD, MP3, magnetic tape, or an electrical storage media such as RAM and ROM or hybrids of these such as magnetic/optical storage media, FLASH media or memory type cards.

Labels or inserts can include identifying information of one or more components therein, dose amounts, clinical pharmacology of the active ingredient(s) including mechanism of action, pharmacokinetics (PK) and pharmacodynamics (PD). Labels or inserts can include information identifying manufacturer information, lot numbers, manufacturer location and date.

Labels or inserts can include information on a condition, disorder, disease or symptom for which a kit component may be used. Labels or inserts can include instructions for the clinician or for a subject for using one or more of the kit components in a method, treatment protocol or therapeutic regimen. Instructions can include dosage amounts, frequency or duration, and instructions for practicing any of the methods or uses, treatment protocols or therapeutic regimes set forth herein. Kits of the invention therefore can additionally include labels or instructions for practicing any of the methods and uses of the invention described herein.

Labels or inserts can include information on any benefit that a component may provide, such as a prophylactic or therapeutic benefit. Labels or inserts can include information on potential adverse side effects, such as warnings to the subject or clinician regarding situations where it would not be appropriate to use a particular composition. Adverse side effects could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Kits can additionally include other components. Each component of the kit can be enclosed within an individual container and all of the various containers can be within a single package. Invention kits can be designed for cold storage.

Representative non-limiting examples of HN and HN analogs/variants that are contemplated in the invention methods, uses and compositions include the following:

Humanin (HN) Analogs and Variants (Tables 1-4)

TABLE 1

HN Variants with characteristics and cytoprotective action

| HN Mutant | Mutation | Characteristics | Cytoprotective Action |
|---|---|---|---|
| HN-F6A | Phe6 to Ala | Loss of IGFBP-3 binding | Similar/more effective than HN |
| HN-S7A or HN-C8A | Ser7 to Ala Cys8 to Ala | Loss of membrane receptor binding | Not effective, prevents HN self-dimerization |

TABLE 1-continued

HN Variants with characteristics and cytoprotective action

| HN Mutant | Mutation | Characteristics | Cytoprotective Action |
|---|---|---|---|
| HN-C8P | Cys8 to Pro | Loss of BAX binding | Not effective, blocks intracellular HN action |
| HN-L12A | Leu12 to Ala | Dimerizes with and inactivates HN | HN antagonist, forms inactive dimer with HN |
| HN-S14G | Ser14 to Gly | Same mechanisms of action as HN | 10 to 1000 more potent than HN in some cells. |

TABLE 2

Additional HN Variants

| Name | Amino acid sequence | SEQ ID NO |
|---|---|---|
| Humanin (HN) | MAPRGFSCLLLLTSEIDLPVKRRA | SEQ ID NO: 1 |
| S14G-HN (HNG) | MAPRGFSCLLLLTGEIDLPVKRRA | SEQ ID NO: 2 |
| D-Ser14 HN | MAPRGFSCLLLLT(DS)EIDLPVKRRA | SEQ ID NO: 3 |
| AGA-HNG | MAPAGASCLLLLTGEIDLPVKRRA | SEQ ID NO: 4 |
| AGA-(D-Ser14)HN | MAPAGASCLLLLT(DS)EIDLPVKRRA | SEQ ID NO: 5 |
| AGA-(D-Ser14)HN17 | PAGASCLLLLT(DS)EIDLP | SEQ ID NO: 6 |
| AGA-(C8R)HNG17 | PAGASRLLLLTGEIDLP | SEQ ID NO: 7 |
| EF-HN | EFLIVIKSMAPRGFSCLLLLTSEIDLPVKRRA | SEQ ID NO: 8 |
| EF-HNG | EFLIVIKSMAPRGFSCLLLLTGEIDLPVKRRA | SEQ ID NO: 9 |
| EF-AGA-HNG | EFLIVIKSMAPAGASCLLLLTGEIDLPVKRRA | SEQ ID NO: 10 |
| Colivelin | SALLRSIPAPAGASRLLLLTGEIDLP | SEQ ID NO: 11 |
| L9R-HN | MAPRGFSCRLLLTSEIDLPVKRRA | SEQ ID NO: 12 |
| Humanin (7) | MTPRGFSCLLLPTSETDLPVKRRX | SEQ ID NO: 13 |
| Humanin (5) | MAPRGFSCLLLSTSEIDLPVKRXX | SEQ ID NO: 14 |
| Humanin (3/11) | MAPRGFSCLLLSTSEIDLPVKRRA | SEQ ID NO: 15 |
| SHLP1 | MCHWAGGASNTGDARGDVFGKQAG | SEQ ID NO: 16 |
| SHLP2 | MGVKFFTLSTRFFPSVQRAVPLWTNS | SEQ ID NO: 17 |
| SHLP3 | MLGYNFSSFPCGTISIAPGFNFYRLYFIWVNGLAKVVW | SEQ ID NO: 18 |
| SHLP4 | MLEVMFLVNRRGKICRVPFTFFNLSL | SEQ ID NO: 19 |
| SHLP5 | MYCSEVGFCSEVAPTEIFNAGLVV | SEQ ID NO: 20 |
| SHLP6 | MLDQDIPMVQPLLKVRLFND | SEQ ID NO: 21 |

TABLE 3

Further HN Variants

| Name | Amino acid sequence | SEQ ID NO |
|---|---|---|
| P-S14 HN 4 | MAPRGFSCLLLLT(p-S)EIDLPVKRRA | SEQ ID NO: 22 |
| P-S7 HN 5 | MAPRGF(p-S)CLLLLTSEIDLPVKRRA | SEQ ID NO: 23 |

TABLE 3-continued

Further HN Variants

| Name | Amino acid sequence | SEQ ID NO |
|---|---|---|
| P-S7/14 HN 6 | MAPRGF(p-S)C TABLE 4-continued

| Name | Amino acid sequence | SEQ ID NO |
|---|---|---|
| AGA-HNG 21 | MAPAGASCLLLLTGEIDLPVKRRA | SEQ ID NO: 4 |
| EF-AGA-HNG 22 | EFLIVIKSMAPAGASCLLLLTGEIDLPVKRRA | SEQ ID NO: 10 |
| HNG-17 23 | PRGFSCLLLLTGEIDLP | SEQ ID NO: 39 |

HNG: An HN derivative, which has a Gly substitution of Ser14 of HN.

HN derivatives can be selected from: Humanin with S14P, P-S7 HN, P-S7/14 HN, (D-Ser14)HN, (D-Ser7)HN, (D-Ser7/14)HN, AGA-(D-Ser14)HN, AGA-(D-Ser14) HN17, EFLIVIKS-HNG, EFLIVIKS-HNA, EFLIVIKS-HN, EFLIVIKS-HNG-KKK, EFLIVIKS-(S7A)HN, and EFLIVIKS-AGA-HNG, and chimeric combinations thereof. The "S14P" means that the S (serine) at location 14 in the wild-type HN has been replaced with P (proline). The same convention applies for other substitutions (e.g., S7A). "D-Ser7" means that the Serine at location 7 has been switched (racemized) from a normal L-isomer to the D-isomer. "AGA-HN" is a shorthand name of the HN derivative in which the Arg4 and Phe6 amino acids are substituted with Alanine to form R4A/F6A-HN (this is named for the AGA triplet at locations 4, 5, and 6 in the HN derivative. "HN17" is a truncated form of HN that includes 17 amino acids from Pro3 to Pro19.

A polypeptide having an amino acid sequence of: Pro-Xn1-(Cys/bXaa)-(Leu/Arg)-Xn2-Leu-Thr-(Gly/Ser)-Xn3-Pro (I) wherein "Cys/bXaa" indicates Cys or a basic amino acid; "(Leu/Arg)" indicates Leu or Arg; "(Gly/Ser)" indicates Gly or Ser, and Xn1, Xn2, and Xn3 independently indicate arbitrary amino acid sequences not more than 10 residues in length, respectively;

A polypeptide having an amino acid sequence of: Pro-Xn1-(Cys/bXaa)-(Leu/Arg)-Xn2-Leu-Thr-(Gly/Ser)-Xn3-Pro (1).

Herein, "Cys/bXaa" indicates Cys or a basic amino acid; "(Leu/Arg)" indicates Leu or Arg; "(Gly/Ser)" indicates Gly or Ser, and Xn1, Xn2, and Xn3 independently indicate arbitrary amino acids not more than 10 residues, respectively.

A polypeptide that has the amino acid sequence of: Pro-(Xaa)1-10-(Cys/bXaa)-(Leu/Arg)-(Xaa)1-10-Leu-Thr-(Gly/Ser)-(Xaa)1-10Pro (wherein Xaa indicates an arbitrary amino acid; "(Xaa)m-n" indicates m to n residues of arbitrary amino acids; "bXaa" indicates a basic amino acid; "Cys/bXaa" indicates Cys or a basic amino acid; "(Leu/Arg)" indicates Leu or Arg; and "(Gly/Ser)" indicates Gly or Ser).

Basic amino acids refer to amino acids in which its R group (side chain) is positively charged at pH7.0. Examples of natural basic amino acids include Arg, Lys, and His.

The amino acid sequences of a polypeptide that has Arg, Lys, or His as the basic amino acids can be represented, for example, as: Pro-Xn1-(Cys/Arg/Lys/His)-(Leu/Arg)-Xn2-Leu-Thr-(Gly/Ser)-Xn3-Pro (wherein "(Cys/Arg/Lys/His)" indicates Cys, Arg, Lys, or His; "(Leu/Arg)" indicates Leu or Arg; "(Gly/Ser)" indicates Gly or Ser; and Xn1, Xn2, and Xn3 independently indicate arbitrary amino acids not more than 10 residues, respectively). Herein, Arg and Lys are particularly preferable as the basic amino acid at this position.

Xn1, Xn2, and Xn3 are independently arbitrary amino acids of 2 to 6, 0 to 4, and 2 to 6 residues, respectively (that is, Xn1=(Xaa)2-6, Xn2=(Xaa)0-4, and Xn3=(Xaa)2-6); more preferably 3 to 5, 1 to 3, and 3 to 5 residues, respectively (that is, Xn1=(Xaa)3-5, Xn2=(Xaa)1-3, and Xn3=(Xaa)3-5); and most preferably 4, 2, and 4 residues, respectively (that is, Xn1=(Xaa)4, Xn2=(Xaa)2, and Xn3=(Xaa)4). Added amino acids of about 6 residues sometimes forms an α-helix and behaves like a single amino acid residue. A polypeptide of the present invention may be a polypeptide wherein arbitrary amino acids with no more than 6 residues are added to all or any one of Xn1, Xn2, and Xn3 consisting of arbitrary amino acids of 4 residues, 2 residues, and 4 residues, respectively.

A sequence of Xn1 includes, for example, sequences consisting of (Arg/Ala)-(Gly/Ala)-(Phe/Ala)-(Ser/Ala), and sequences with conservative substitution thereof. Herein, for example, "Arg/Ala" indicates Arg or Ala ("/" indicates that it is either one of the residues; the same is indicated throughout the description herein). Examples of such sequences include Arg-Gly-Phe-Ser, Ala-Gly-Phe-Ser, Arg-Ala-Phe-Ser, Arg-Gly-Ala-Ser, Arg-Gly-Phe-Ala, and so on. Other examples include Arg-Gly-Ala-Ala, Arg-Ala-Phe-Ala, Arg-Ala-Ala-Ser, Arg-Ala-Ala-Ala, Ala-Gly-Phe-Ala, Ala-Gly-Ala-Ser, Ala-Gly-Ala-Ala, Ala-Ala-Phe-Ser, Ala-Ala-Phe-Ala, Ala-Ala-Ala-Ser, Ala-Ala-Ala-Ala, and such.

Conservative substitution can be exemplified by substitution within a group of amino acids, corresponding to conservative substitution, which will be described later. On the other hand, the sequence of Xn2 preferably includes, for example, sequences consisting of (Leu/Ala)-(Leu/Ala), and sequences with conservative substitution thereof. Such sequences include Leu-Leu, Ala-Leu, Leu-Ala, and such. Ala-Ala can be also exemplified as such sequences. Furthermore, the sequence of Xn3 preferably includes, for example, sequences consisting of (Glu/Ala)-(Ile/Ala)-(Asp/Ala)-(Leu/Ala), and sequences with conservative substitution thereof. Such examples include Glu-Ile-Asp-Leu, Ala-Ile-Asp-Leu, Glu-Ala-Asp-Leu, Glu-Ile-Ala-Leu, Glu-Ile-Asp-Ala, and so on. Other examples are Glu-Ile-Ala-Ala, Glu-Ala-Asp-Ala, Glu-Ala-Ala-Leu, Glu-Ala-Ala-Ala, Ala-Ile-Asp-Ala, Ala-Ile-Ala-Leu, Ala-Ile-Ala-Ala, Ala-Ala-Asp-Leu, Ala-Ala-Asp-Ala, Ala-Ala-Ala-Leu, Ala-Ala-Ala-Ala, and so on. The sequences of Xn1, Xn2, and Xn3 may be selected from arbitrary combinations.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All applications, publications, patents and other references, GenBank citations and ATCC citations cited herein are incorporated by reference in their entirety. In case of conflict, the specification, including definitions, will control.

All of the features disclosed herein may be combined in any combination. Each feature disclosed in the specification may be replaced by an alternative feature serving a same, equivalent, or similar purpose. Thus, unless expressly stated otherwise, disclosed features (e.g., humanin and humanin analogs) are an example of a genus of equivalent or similar features.

As used herein, the singular forms "a," "and," and "the" include plural referents unless the context clearly indicates otherwise. Thus, for example, reference to "a humanin" includes a plurality of humanin molecules. In addition, reference to an anti-cancer or anti-tumor therapeutic agent includes a plurality of anti-cancer or anti-tumor therapeutic agents.

As used herein, all numerical values or numerical ranges include integers within such ranges and fractions of the values or the integers within ranges unless the context clearly indicates otherwise. Thus, to illustrate, reference to at least 100%, includes 101%, 102%, 103%, 104%, 105%, etc., as well as 101.1%, 101.2%, 101.3%, 101.4%, 101.5%, etc.

Reference to an integer with more (greater) or less than includes any number greater or less than the reference number, respectively. Thus, for example, a reference to less than 1,000, includes 999, 998, 997, etc. all the way down to the number one (1), and fractions thereof (e.g., 0.5, 0.1, 0.05, 0.01, etc.; and less than 100, includes 99, 98, 97, etc. all the way down to the number one (1), and fractions thereof (e.g., 0.5, 0.1, 0.05, 0.01, etc.).

As used herein, all numerical values or ranges include fractions of the values and integers within such ranges and fractions of the integers within such ranges unless the context clearly indicates otherwise. Thus, to illustrate, reference to a numerical range, such as a percentage range, such as 50-100 includes 51, 52, 53, 54, 55, 56, 57, 58, 59, 60, as well as 51.1, 51.2, 51.3, 51.4, 51.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth.

Reference to a series of ranges includes ranges which combine the values of the boundaries of different ranges within the series. Thus, to illustrate reference to a series of ranges of 11-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, 4,500-5,000, 5,500-6,000, 6,000-7,000, 7,000-8,000, or 8,000-9,000, includes ranges of 10-50, 50-100, 100-1,000, 1,000-3,000, 2,000-4,000, etc.

The invention is generally disclosed herein using affirmative language to describe the numerous embodiments and aspects. The invention also specifically includes embodiments in which particular subject matter is excluded, in full or in part, such as substances or materials, method steps and conditions, protocols, or procedures. For example, in certain embodiments or aspects of the invention, materials and/or method steps are excluded. Thus, even though the invention is generally not expressed herein in terms of what the invention does not include aspects that are not expressly excluded in the invention are nevertheless disclosed herein.

A number of embodiments of the invention have been described. Nevertheless, one skilled in the art, without departing from the spirit and scope of the invention, can make various changes and modifications of the invention to adapt it to various usages and conditions. Accordingly, the following examples are intended to illustrate but not limit the scope of the invention claimed.

EXAMPLES

Example 1

1. Materials and Methods

B16 Melanoma Cells Culture:

Mouse B16 melanoma cells were cultured in 75 $cm^2$ flasks and incubated at 37° C. in a humidified chamber with 5% $CO_2$ to generate enough cells for inoculating 10,000 cells/mouse×40 mice. After 5-7 days culture, B16 cells were collected and cell viability determined using the Trypan Blue stain and the number of living cells were counted under microscope.

Treatment Schedule: 7 weeks old C57BL/6 male mouse, control without tumor inoculation (n=6) and four other groups (n=10 each group) received B16 tumor cells (10,000/mouse) injection under the skin in the right flank. One group was not treated; another group received HNG IP injection, 5 mg/Kg BM, daily×40 days (HNG); the third group received Doxorubicin (DOX), IP injection, 5 mg/Kg BW, weekly×6 injections; and the last group DOX+HNG (Table 5).

TABLE 5

DOX ± HNG in B16 cell transplanted mice study

| Groups (n) | Tumor Inoculation | Treatment |
|---|---|---|
| Control (6) | no | Vehicle |
| Not treated (10) | + | Vehicle |
| DOX (10) | + | DOX (5 mg/Kg, weekly × 6 injections) |
| HNG (10) | + | HNG (5 mg/Kg, daily × 40 days) |
| DOX + HNG (10) | + | DOX + HNG |

2. Sample and Data Collection

FIG. 1 shows the schedule of events for this study. The mice in the DOX treated group would receive 6 weekly injections of DOX and daily injection of HNG until Day 40. Body weights and tumor cell injection site were checked 3 times per week. Echocardiogram was scheduled at day 26 and repeated at day 40. Twenty four hours after echocardiogram examination, animals were sacrificed; whole blood, plasma, epididymis, heart, lung, testis, liver, spleen, kidney, intestine, muscle, skin, and femur bone were collected. Sperm in the cauda epididymis were counted and COMET assay for DNA damage of sperm assessed. Whole blood was collected for CBC analysis and plasma saved for measurement of HNG level or other bio-parameters. Testes were fixed in Bouin's or formaldehyde for immunohistochemistry and TUNEL analyses.

The heart containing left and right ventricles were fixed with formalin for hematoxylin/eosin and trichrome staining and TUNEL to detect apoptotic cell. Heart sections were saved for immunohistochemistry. Pieces of left ventricle were fixed with gluteraldehyde for later mitochondria analysis by EM. Heart was snapped frozen and stored at −80 degrees (left and right atriums plus the rest of ventricles) for molecular studies (e.g. ANP/BNP).

3. Results

Body Weight:

FIG. 2 shows that the control, untreated, and HNG treatment mice gained weight. However the DOX and DOX+HNG mice started to lose weight at about day 8 to 10. At day 29, DOX group lost more weight than the mice treated with DOX+HNG ($p<0.05$).

Heterotopic Subcutaneously Implanted Melanoma:

Because only $10^4$ cells were inoculated, none of the mice injected with the tumor cells had a tumor at the injection site or other areas of the body. These tumor cells died and were phagocytosed by the host.

Outcome of the Mice:

The mice treated with DOX had significant loss in weight after the 4$^{th}$ DOX injection on day 23. The DOX injections were halted and the animals were observed for cardiotoxicity. The DOX and DOX+HNG groups were scheduled for echocardiogram on day 32, but three mice in the DOX group died on day 31 and another on day 32 after completing the echocardiogram, another on day 33 and the 6$^{th}$ died on day 37. All but one (which died on day 38) of the mice treated with DOX+HNG survived, though their weight was lower than the non-treated and HNG treated group. These results indicate that HNG protected the DOX treated animals from death (DOX alone 4/10 survived; DOX+HNG 9/10 survived).

Figure 3A:
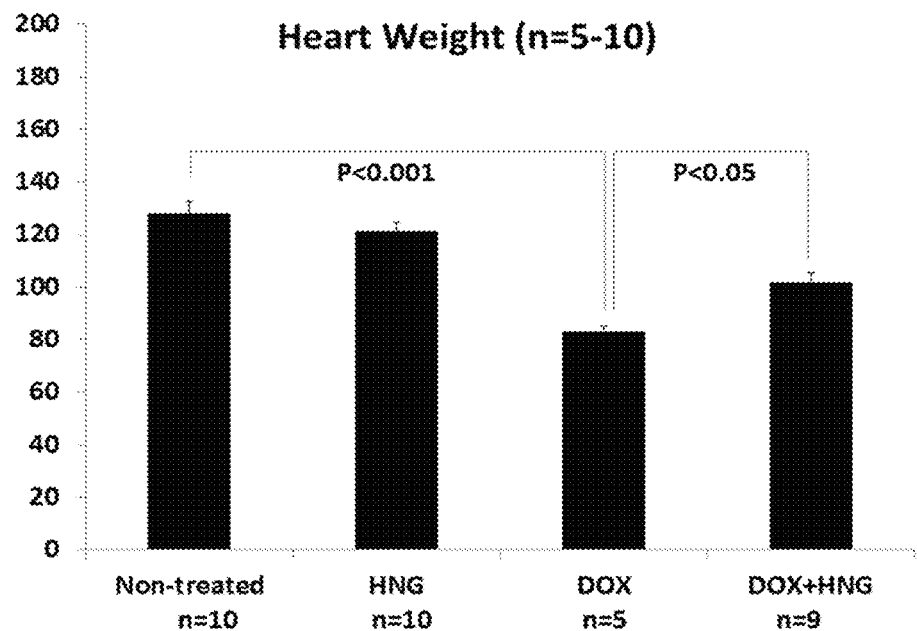
FIG. 3A shows a graphical summary of heart weight (mg, y-axis).
Figure 3B:
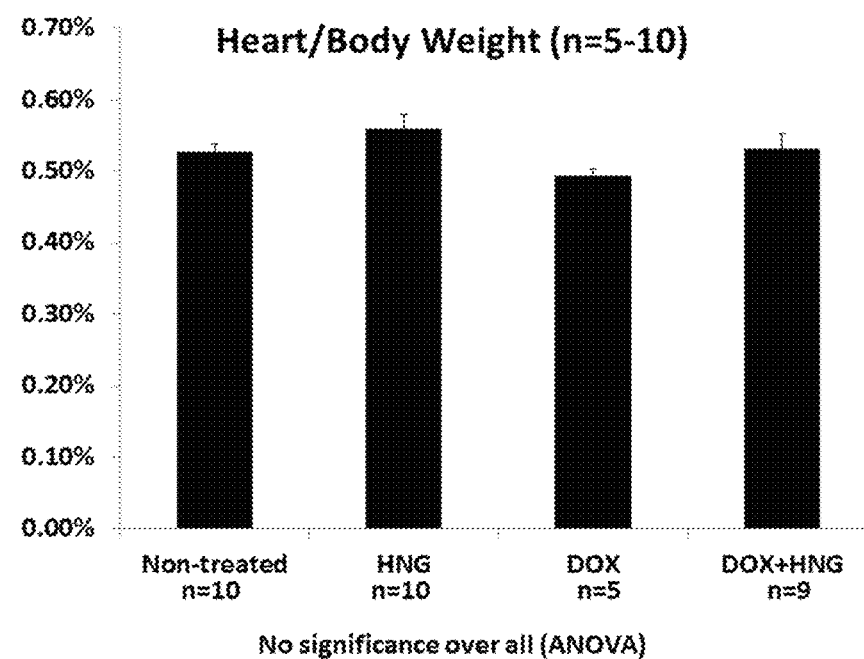
FIG. 3B shows a graphical summary of percentages of heart weight to body weight (y-axis) for untreated and treated mice as indicated on the x-axis. Mice treated with DOX had smaller hearts than non-treated and HNG treated mice, HNG+DOX had significantly higher heart weight than DOX alone group. When corrected by body weight, these differences were still observed.

Heart and Echocardiogram Analyses:

Echocardiogram was performed on three mice from each group on day 32, and the rest of the mice on days 34 and 38. The weight of the heart of the DOX treated mice was significantly lower than the non-treated and HNG treated mice ($p<0.001$). Heart weight in the HNG+DOX group was significantly higher than the DOX only group ($p<0.05$). However when corrected for body weight, the heart: body weight ratio was not different among the groups (FIGS. 3A & 3B.)

Figure 4A:
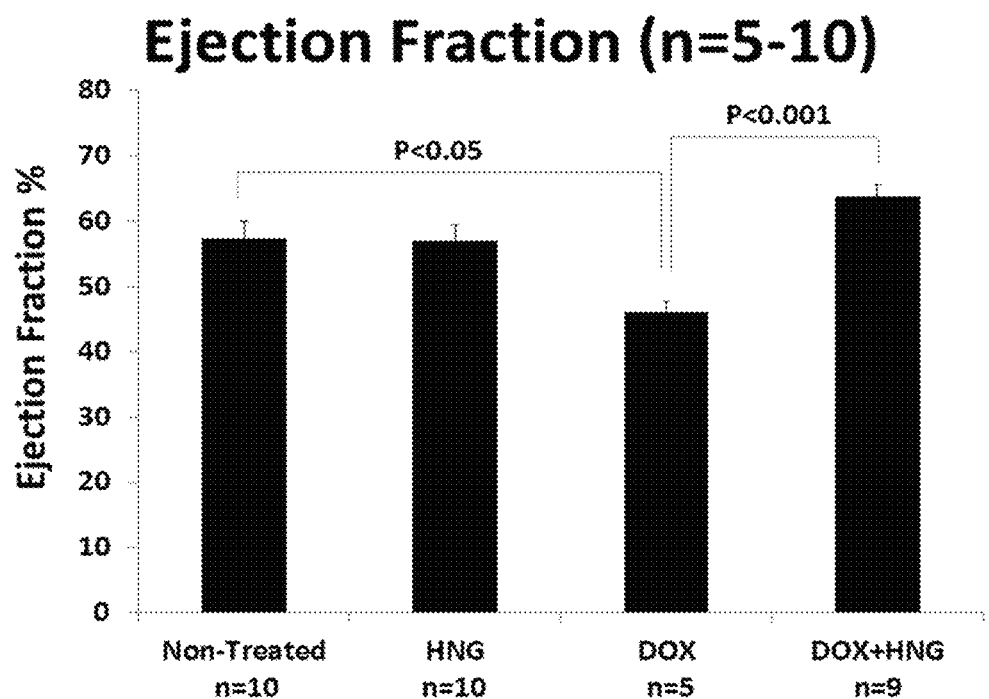
FIG. 4A shows mice treated with DOX had lower ejection fraction.
Figure 4B:
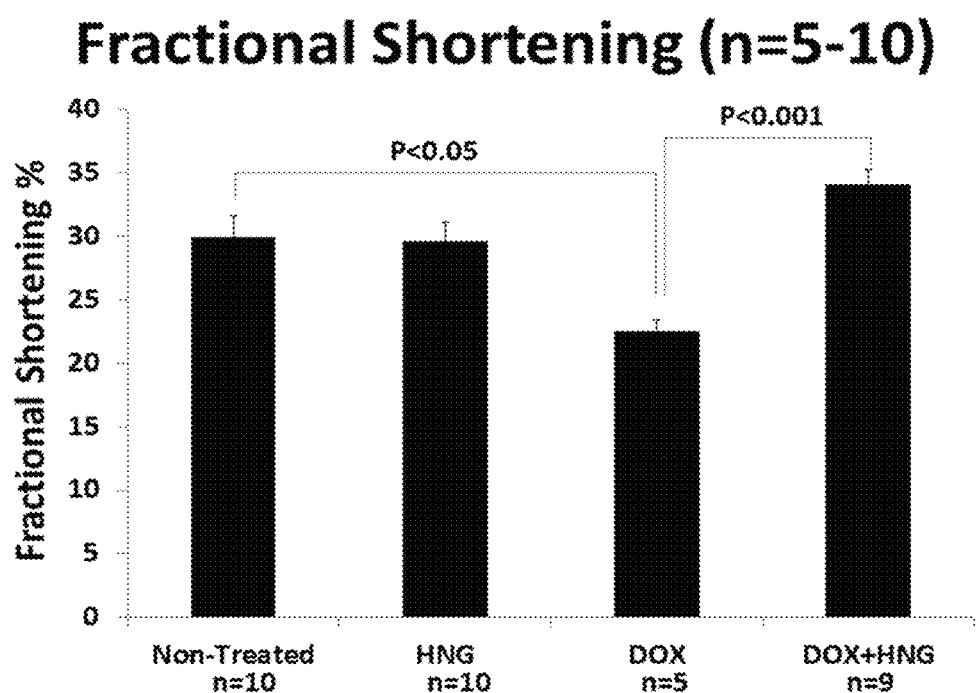
FIG. 4B shows mice treated with DOX had lower fractional shortening. Both parameters were improved by co-administration.

Cardiac function of the DOX treated mice was significantly impaired with a decrease in ejection fraction and fractional ventricular shortening compared to non-treated and HNG treated mice. Co-treatment with HNG returned these DOX induced cardiac function parameters to normal (untreated mice) (FIGS. 4A & 4B).

4. Conclusion

The foregoing studies showed that HNG decreases DOX-induced weight loss and promotes survival in mice treated with DOX. HNG protects mice from the cardiotoxicity induced by DOX. Currently there is no treatment for DOX-induced cardiotoxicity except for dexrazoxane which is recommended for patients receiving high doses of anthracyclines. However, dexrazoxane causes significant adverse events including decreased granulocytes and platelets. Co-administration of humanin or its analogs may have a potential role in ameliorating anthracycline-induced cardiomyopathy and chronic recurrent heart failure.

Example 2

Figure 5:
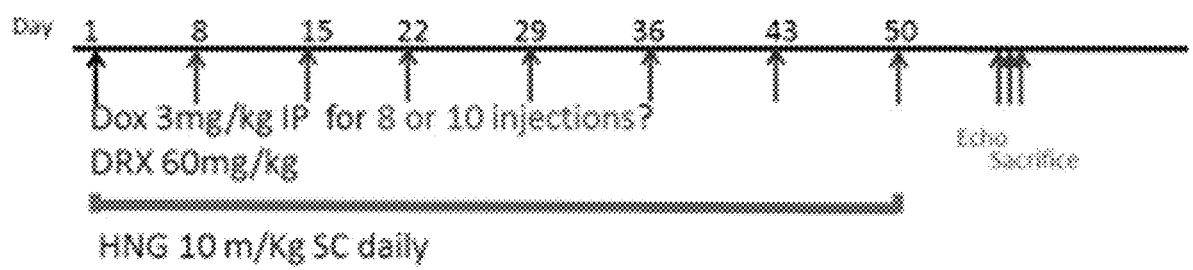
FIG. 5 shows an experimental design and treatment schedule. Echocardiograms were performed on 20 to 30 mice a day for 3 or 4 days on at week 4, 8 and 10. Animals were sacrificed at week 10. N=10 per group. Mice were 10 week old C57/B6 mice. There were 6 groups: Control, HNG (5 mg/day, IP), Dox (3 mg/week, IP), Dox+HNG, Dexrazoxane (DRX, 60 mg/week, IP), Dox+DRX and DRX+HNG.

Experimental Design (FIG. 5).

In this second experiment, adult male mice were used. These mice received for 8 weeks IP injections of saline daily (control), Doxorubicin (DOX 3 mg/week IP for 8 injections), HNG 5 mg/day IP), Dexrazoxane (DRZ 60 mg/week IP at the same time as Doxorubicin) either alone or in combinations as shown in FIG. 5. All animals received 8 weeks of injections. The DOX injections were stopped after 8 injections because the animals showed signs of ill health, and all treatment was stopped at week 9 and mice were sacrificed at week 10 after echocardiogram.

Results

Figure 6:
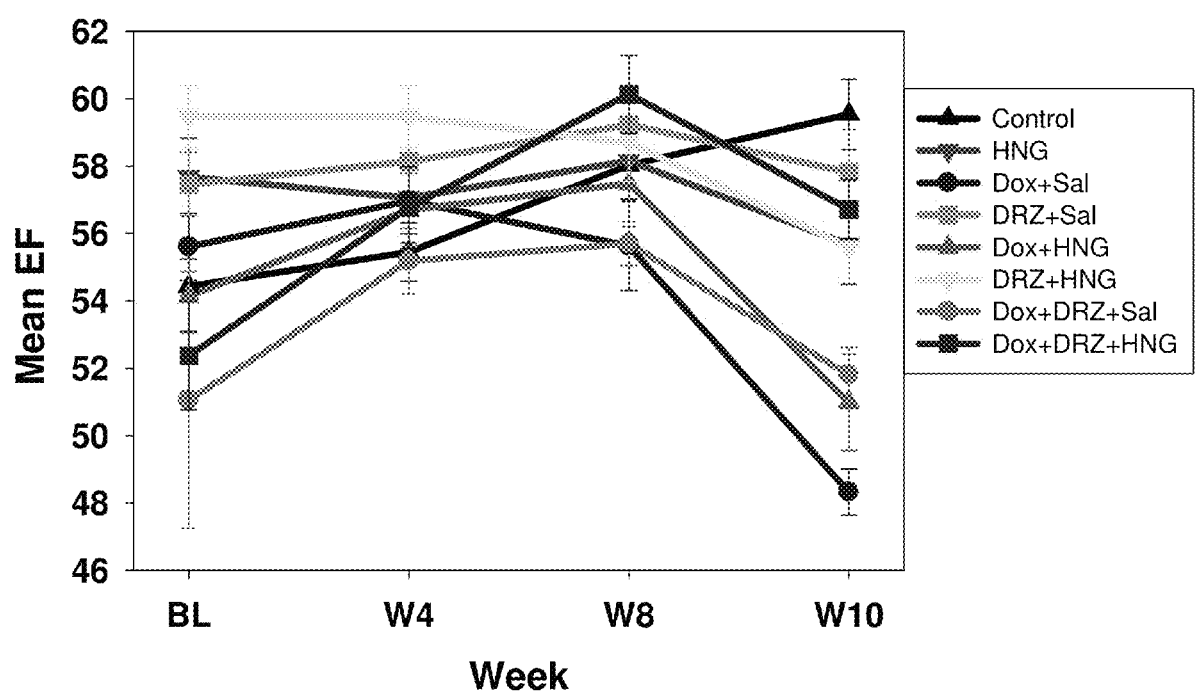
FIG. 6 shows ejection mean fraction (y-axis) after treatment with Dox, HNG and DRZ alone or in combinations.

The results of the analyses of the ejections fraction is shown in FIG. 6. Ejection fraction (EF) of the groups were not different at baseline, week and week 8 amongst the groups. Dox treatment caused a highly significant decrease in EF compared to control, HNG alone, DRZ alone ($p<0.0001$). The decrease in EF was ameliorated with DRZ ($p=0.029$) and HNG ($p=0.07$ because of larger variation in this group). The combination of DRZ and HNG markedly reduced the DOX-induced lowering of EF ($p<0.0001$) and was more effective than DRZ ($p=0.003$) and HNG ($p=0.001$). The combined treatment with HNG and DRZ restored the DOX induced decrease in EF to control levels.

Conclusion

Our second experiment showed that as previously shown DRX decreased the DOX induced cardiotoxicity. HNG showed the same trend in decreasing DOX induced loss of EF. However most strikingly the combined treatment of DRX+HNG completely reversed the cardiotoxic effect of DOX on cardiac ejections fraction better that either DRZ or HNG treatment. DRZ has been shown to induce testicular toxicity where HNG protects the testis form chemotherapeutic injury. Thus our experiments confirm that HNG alone or together with DRZ may protect the toxic effect of DOX on the heart.

Example 3

Dox treatment results in subclinical, progressive, irreversible cardiotoxicity causing significant morbidity and mortality in cancer survivors. Dox also induces myocardial damage and dysfunction by stimulating reactive oxygen species (ROS) production by affecting redox homeostasis. In addition, free cellular iron forming toxic Dox-iron complexes generate ROS resulting in mitochondrial dysfunction. Dox binds both DNA and topoisomerase 2 isoenzymes to forms ternary Top2-Dox-DNA cleavage complex, triggering DNA breaks. When Dox binds to Top2α, it inhibits DNA replication, results in cell cycle arrest and apoptosis of cancer cells. However, when Dox binds to Top2β in cardiomyocytes, it impairs calcium handling and causes mitochondrial dysfunction and subsequent cardiomyocyte apoptosis. The data presented herein suggests that mitochondria may be a primary targets of Dox-induced cardiotoxicity.

The objectives of this study was to investigate whether HNG alone or in combination with DRZ can 1) prevent Dox-induced cardiac dysfunction; and/or 2) ameliorate Dox-induced mitochondrial damage in the heart.

Materials and Methods

Animals and Reagents

Young adult [10-week-old; body weight (BW), 24-28 g] male mice (C57BL/6J) purchased from the Jackson Laboratory (Bar Harbor, Me.) were housed in a standard animal facility under controlled temperature (22° C.) and photoperiod (12 h light, 12 h dark) with free access to water and mouse chow. Animal handling and experimentation were in accordance with the recommendations of the American Veterinary Medical Association and approved by the Los Angeles Biomedical Research Institute at Harbor-University of California-Los Angeles (UCLA) Medical Center Animal Care and Use Review Committee (IACUC) and UCLA-IACUC. Doxorubicin (Dox) and Dexrazoxane (DRZ) were obtained from Tocris Bioscience (Bristol, UK) and dissolved in saline at concentration of 1 mg/ml for Dox and 9 mg/ml for DRZ before use. Humanin analogue HNG was synthesized by CPC Scientific (Sunnyvale, Calif.) and dissolved in saline at concentration of 1 mg/ml just before use.

Study Design

A total of 80 adult male mice were randomly divided into 8 groups (10 mice per group) to receive the following treatment via intraperitoneal injection (i.p.): Group 1 (Control) daily saline injection; Group 2 (HNG) 5 mg/kg of HNG daily; Group 3 (Dox) 3 mg/kg of Dox weekly; Group 4

(DRZ) 60 mg/kg of DRZ weekly; Group 5 (DRZ+HNG); Group 6 (DOX+HNG); Group 7 (Dox+DRZ); and Group 8 (Dox+HNG+DRZ) treatment. The selected doses of HNG (5 mg/kg/day), Dox (3 mg/kg/week) and DRZ (60 mg/kg/week) were based on previous mice models to study HNG cytoprotection and Dox cardiotoxicity. Mice received 8 doses of either Dox or DRZ or Dox+DRZ weekly injection for 7 weeks, and daily HNG injection for 10 weeks. To monitor cardiac function, an echocardiogram was performed at baseline and repeated at 4, 8 and 9.5 weeks after the first injection of Dox, DRZ, and HNG, alone or in combinations. Dose adjustment of all drugs was based on weekly BW of each mouse. Mice were euthanized with i.p. injection of pentobarbital (200 mg/kg BW) at the end of 10 weeks. Blood samples were collected from the left ventricle, and hearts were harvested, weighted and divided into 3 portions by transverse sections through both right and left ventricles: one portion was immersed into 10% buffered formalin (Fisher Scientific), processed for histological examination, and assessing cardiomyocyte apoptosis and fibrosis; another portion was snap-frozen into liquid nitrogen for RNA isolation, qRT-PCR array and Qt-PCR; and the remaining portion was frozen for protein isolation and analyses.

Echocardiography

Echocardiography was performed. The animals were under 1.5% isoflurane anesthesia. The echocardiography was performed using a Vevo2100 ultrasound system (VisualSonics, Inc., Toronto, ON, Canada). A parasternal long-axis B-mode image was obtained by positioning the probe parallel to the long-axis of the left ventricle (LV) with the ultrasound beam running perpendicular to the left ventricle. The probe was rotated at 90° to obtain a parasternal short-axis view of the left ventricle. The papillary muscle was used as a standard to ensure reproducible and similar images between the animals. Using this short axis view, an M-mode short video clip was stored to document LV dimensions for further analysis. Echocardiographic parameters for ejection fraction (EF) images were analyzed using the Vevo2100 cardiac analysis package.

Quantification of Cardiomyocyte Apoptosis by Co-Localization of Tropomyosin and DNA Fragmentation Formalin-fixed and paraffin-embedded transverse ventricular heart sections from each mouse were used to co-localize expression of tropomyosin, a myocardium marker, and terminal deoxynucleotidyl transferase dUTP nick end labeling (TUNEL) for detection of apoptosis. Apoptosis was quantified in 6 mice per group and expressed as apoptotic index (AI), which was the number of TUNEL positive apoptotic cardiomyocytes per the number of cardiomyocyte nuclei in left ventricular sections. Under fluorescent microscope, 10 areas were randomly selected under the magnification of 200, and a total of 3000 cardiomyocyte nuclei were counted per mouse heart.

RNA Extraction from Cardiac Tissue, Reverse Transcription and Real-Time PCR

Total RNA was extracted from left ventricular tissue using TRIzol reagent (Life Technologies, NY, USA). 1 µg RNA was reverse-transcribed into first-strand cDNA using ProtoScript II Reverse Transcriptase (New England BioLabs) and Random Primer (Life Technologies, NY, USA). Real-time PCR was performed using the CFX96 Real-Time PCR Detection System (Bio-Rad, CA, USA) using the iQ SYBR Green Supermix (Bio-Rad). Values were normalized to beta-actin to calculate relative expression levels. The primers used for Qt-PCR were 1) Atrial Natriuretic Factor (ANF): mANF RT-F: AGGCAGTCGATTCTGCTTGA (SEQ ID NO:40); mANF RT-R: CGTGATAGAT-GAAGGCAGGAAG (SEQ ID NO:41); and 2) beta-actin: mActB RT-F: TGGCACCACACCTTCTACAA (SEQ ID NO:42); mActB RT-R: GTCTCCGGAGTCCATCACAA (SEQ ID NO:43).

Trichrome Staining and Quantification of Fibrosis in Hearts

Formalin-fixed and paraffin-embedded transverse ventricular heart sections from 6 mice per group were stained with Masson's Trichrome procedures. Images of the Trichrome stained sections of left ventricles were made at 200 magnification using Nikon Eclipse, TE 2000-U microscope. The images were analyzed for percent fibrosis per heart using Nikon Image System Elements AR program. Fibrosis area was designated by blue staining, and the total tissue images were designated by both red and blue. The fibrosis response was quantified by a percentage of blue area over total area assessed.

qRT-PCR Array and Date Analysis

Nuclear-gene-encoded mRNA for mitochondrial proteins of 4 mouse hearts from the control, Dox only, and Dox+HNG+DRZ treated groups were assessed by mitochondrial gene focused RT-PCR array (PAMM-087ZC RT2 Profiler™ PCR array, Qiagen, Hilden, Germany). Total RNA was extracted from cardiac left ventricular tissue using an RNeasy Fibrous Tissue Mini Kit (Qiagen, Hilden, Germany). RNA concentration was measured by NannoDrop 2000 Spectrophotometer (ThermoFisher Scientific, Waltham, USA). The isolated RNA from each heart was reverse transcribed into cDNA using RT2 First Strand Kit (Qiagen, Hilden, Germany). The cDNA was then mixed with RT2 SYBR Green ROX qPCR Mastermix, placed into a mouse mitochondrial gene array, and subjected to run the real-time PCR cycling program (ABI one step plus real time PCR system) to detect 84 nuclear-gene-encoded mitochondrial gene expression. Gene expression data generated from arrays were analyzed by Qiagen Software, and compared among the control and treated groups.

Protein Extraction and Protein-Simple Assay

Left ventricle samples from mice were sonicated in RIPA buffer (Sigma) supplemented with EDTA-free protease inhibitor cocktail tablets (Roche), and cell debris removed by centrifugation. The protein concentration was analyzed by Bio-Rad Protein Assay and measured by Beckman Du-640 Spectrophotometer.

Protein measurement for the uncoupling protein 2 (Ucp2) was performed using ventricle tissue lysates from control, Dox only, Dox+HNG, Dox+DRZ, and Dox+HNG+DRZ treated mice. Protein expression was quantified by Wes Separation Module with 25 Capillary Cartridges for 12-230 kDa (Wes®). Proteins (4 microgram/sample) were separated through a size-resolving matrix in capillaries, immobilized to the inner capillary wall, incubated with anti-Ucp2 rabbit monoclonal antibody (Cell Signaling) at concentration of 1 µg/ml and anti-rabbit secondary antibodies before detection using chemiluminescence. Signals reflected as the area under the curve of Ucp2 protein were generated automatically at the end of the run. The Ucp2 protein levels were quantified by a ratio of the area under the curve from each sample that was normalized by the corresponding area under the curve of the corresponding total protein.

Statistical Analysis

Effects of HNG+DRZ+Dox vs Dox and HNG or DRZ vs Dox treated mice were compared. Statistical analyses were carried out using the SigmaStat 12.0 Program (Systat Software, Inc.). Results were tested for statistical significance using one-way ANOVA with post hoc Tukey test or Student's t test. For fibrosis quantification, the p value was calculated using Duncan's multiple comparison tests. Differences were considered significant if p<0.05.

Outcome and General Health of Treated Mice

Figure 7A:
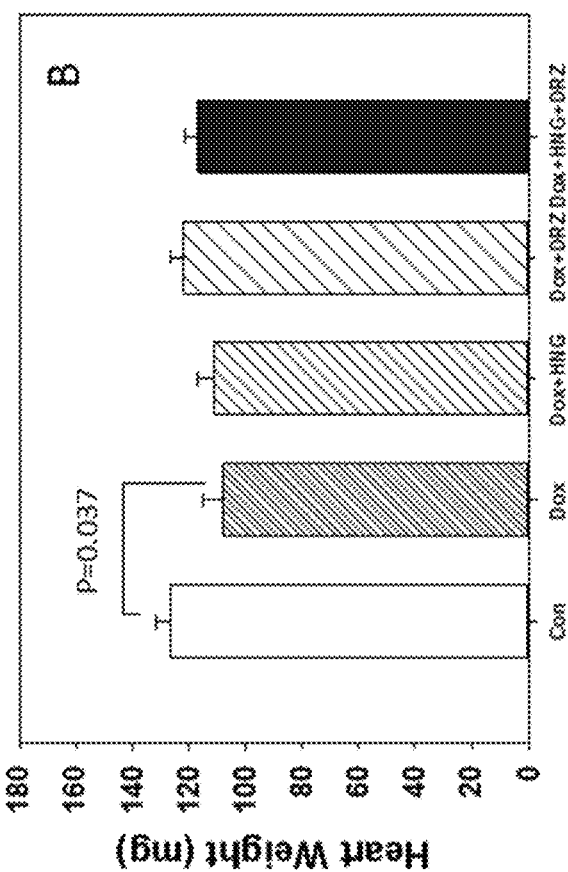
FIG. 7A shows body weight from control, Dox alone, Dox+HNG, Dox+DRZ, and Dox+HNG+DRZ treated mice as indicated at the bottom of each figure.
Figure 7B:
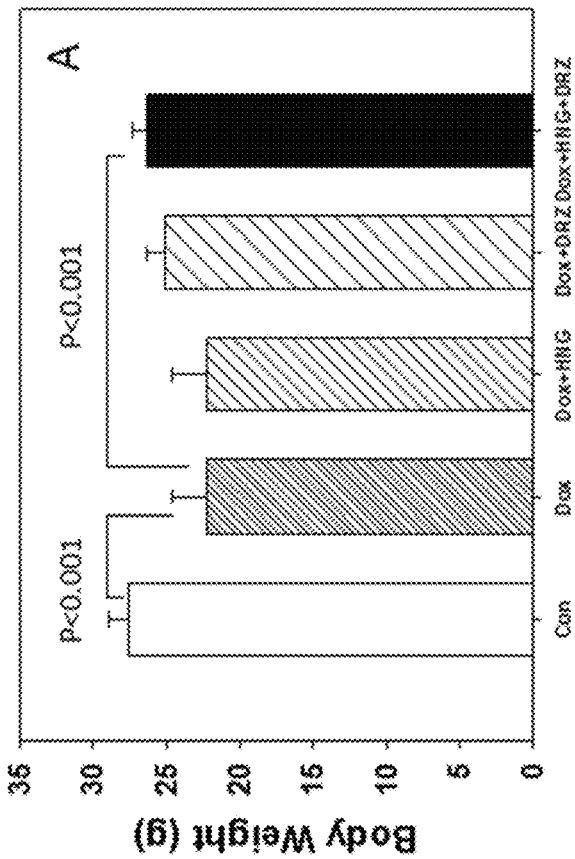
FIG. 7B shows heart weight from control, Dox alone, Dox+HNG, Dox+DRZ, and Dox+HNG+DRZ treated mice as indicated at the bottom of each figure.
Figure 15A:
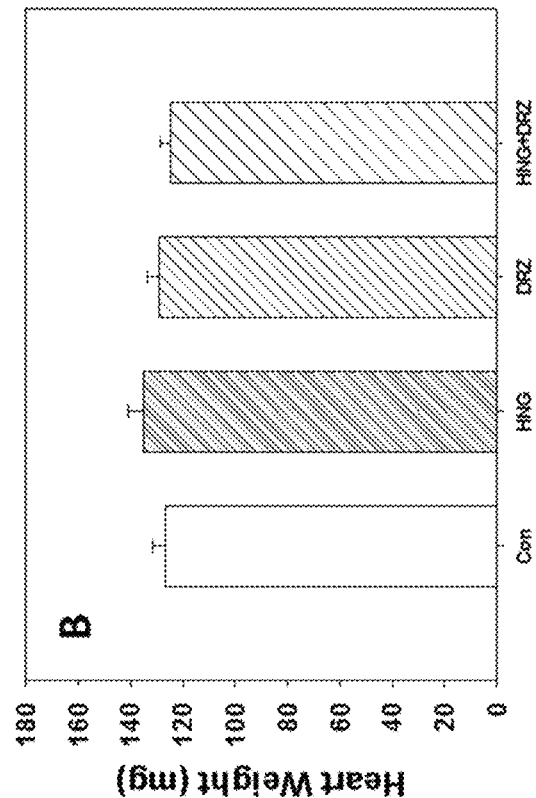
FIG. 15A shows body weight from control, HNG, DRZ, and HNG+DRZ treated mice.
Figure 15B:
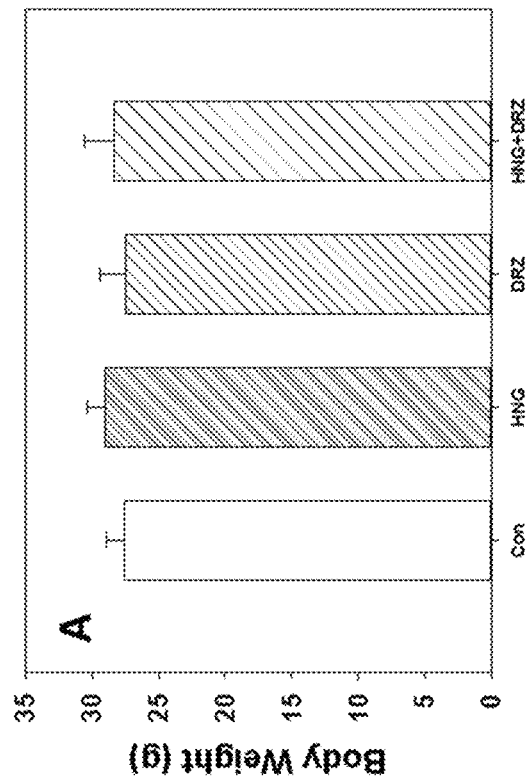
FIG. 15B shows heart weight from control, HNG, DRZ, and HNG+DRZ treated mice.
Figure 16A:
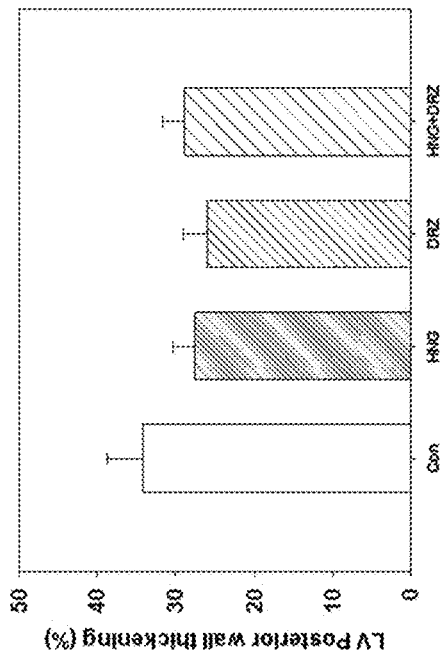
FIGS. 16A-D show a graphical summary of FIG. 16A heart rate, FIG. 16B left ventricle posterior wall thickening, FIG. 16C fractional shortening, and FIG. 16D ejection fraction measured by M-mode echocardiography in control, HNG, DRZ and HNG+DRZ treated mice.
Figure 16B:
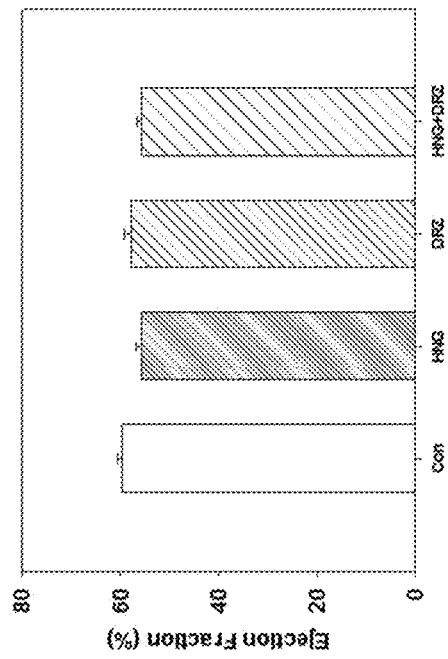
Figure 16C:
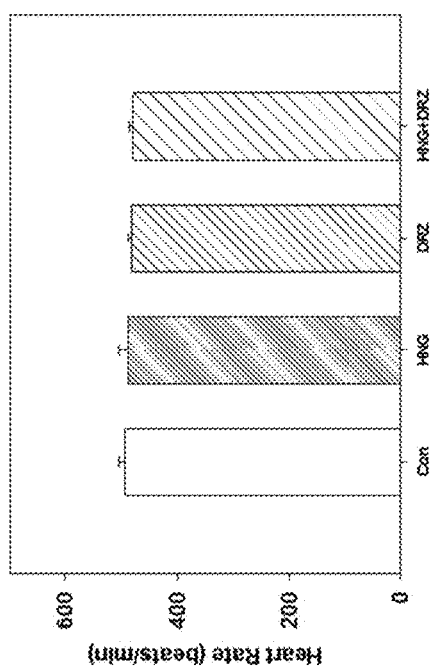
Figure 16D:
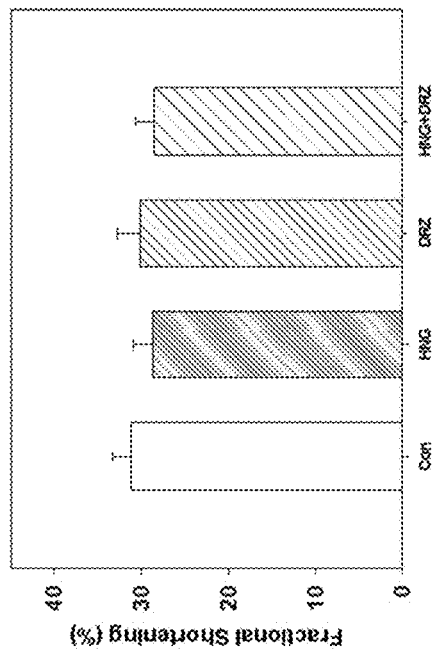

Seventy-one out of 80 mice survived until the end of this study. Nine mice died before the termination of the experiment: one from the control group died at week 8 of unknown cause; two from the Dox+DRZ group died at week 2 and 10 respectively; three from the Dox treated group died at week 9 and three from the Dox+HNG group died at week 10. The cause of death in Dox-treated mice was most likely related to the general toxicity of Dox. At the end of 10 weeks in survival mice, HNG, DRZ or HNG+DRZ had no significant adverse effect on body weight (BW) (FIGS. 15A and 15B). Dox treatment significantly decreased body weight (BW) as compared to the control mice. While HNG or DRZ in Dox-treated mice attenuated the Dox-induced BW loss, combined treatment of HNG+DRZ+Dox restored body weight to near control level (FIG. 7A). Dox alone significantly decreased heart weight by 14% compared to the control mice, in contrast there were no significant changes in heart weight among control, Dox+HNG, Dox+DRZ and Dox+HNG+DRZ treated mice (FIG. 7B).

Dox-Induced Cardiac Dysfunction

Figure 10:
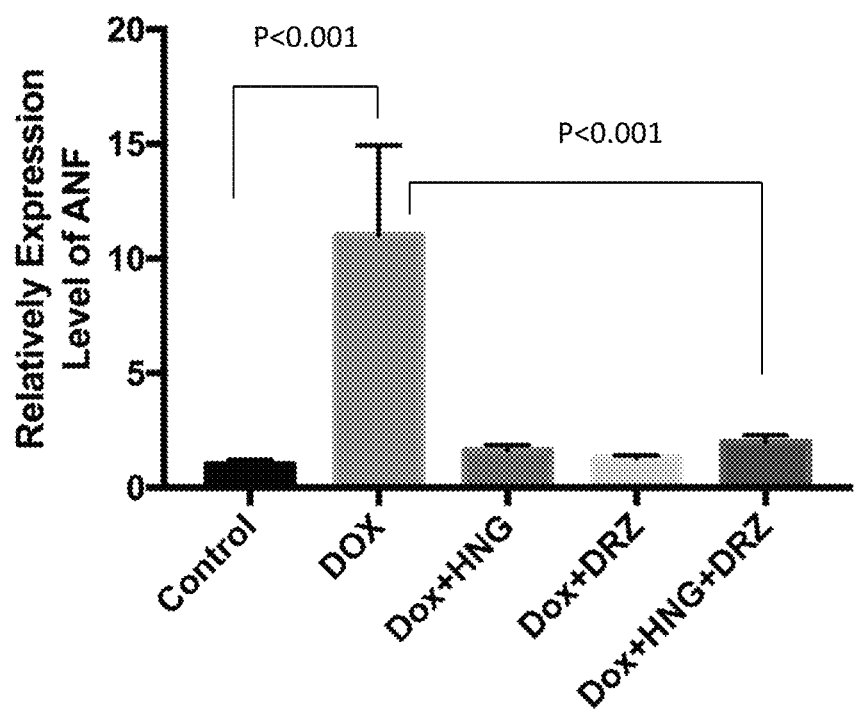
FIG. 10 shows relative expression levels of ANF transcripts (y-axis) in saline control (Control), Dox, Dox+HNG, Dox+DRZ and Dox+HNG+DRZ treated mice as indicated at the bottom of the graph.
Figure 17A:
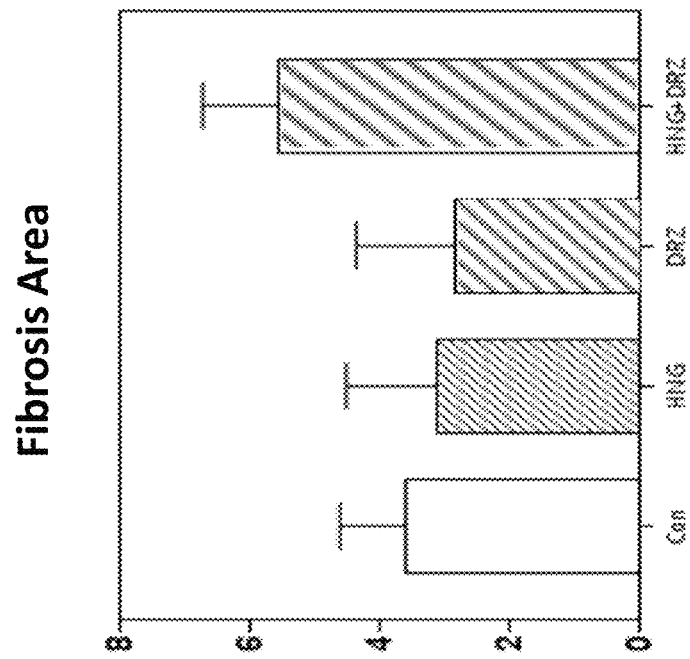
FIG. 17A shows expression levels of ANF transcripts in control, HNG, DRZ, and HNG+DRZ treated mouse hearts.

HNG, DRZ or DRZ+HNG treatment mice did not show any altered cardiac parameters measured as compared to controls across the treatment period (FIG. 16). Dox treatment alone significantly decreased heart rate (FIG. 9A), left ventricle posterior wall thickness (FIG. 9B), fractional shortening (FIG. 9C), and ejection fraction (FIG. 9D) at 9.5 weeks after treatment. HNG+Dox treatment significantly attenuated the loss of left ventricle posterior wall thickening, but did not affect the other parameters (heart rate, fractional shortening, and ejection fraction) as compared to Dox treatment alone. DRZ+Dox treatment significantly ameliorated the Dox-induced decreases in the left ventricle posterior wall thickening and ejection fraction. Most importantly, combined treatment of HNG+DRZ+Dox restored heart rate, left ventricle posterior wall thickening, fractional shortening, and ejection fraction to control levels. While DRZ, HNG or DRZ+HNG only treatment did not significantly altered ANF transcripts (FIG. 17A), the expression levels of ANF mRNA, a heart failure biomarker, were significantly increased in Dox only treated hearts; the addition of HNG, DRZ or combined HNG+DRZ to Dox-treated mice returned expression of ANF to control levels (FIG. 10).

DOX-Induced Cardiomyocyte Apoptosis

Figure 11A:
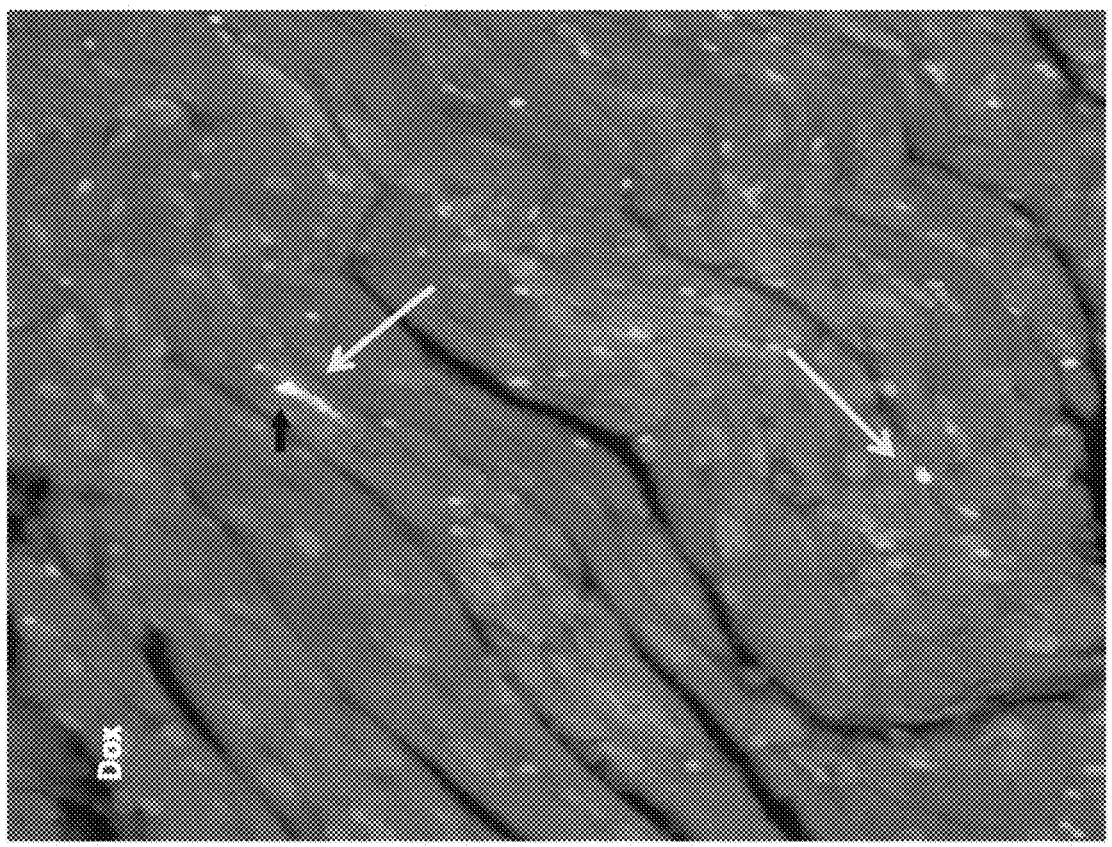
FIGS. 11A-C show photomicrographs of immunohistochemistry staining of mouse heart tissue showing Tropomyosin as red fluorescence, and TUNEL positive cells as green fluorescence from FIG. 11A control and FIG. 11B Dox+HNG+DRZ treated mice.
Figure 11B:
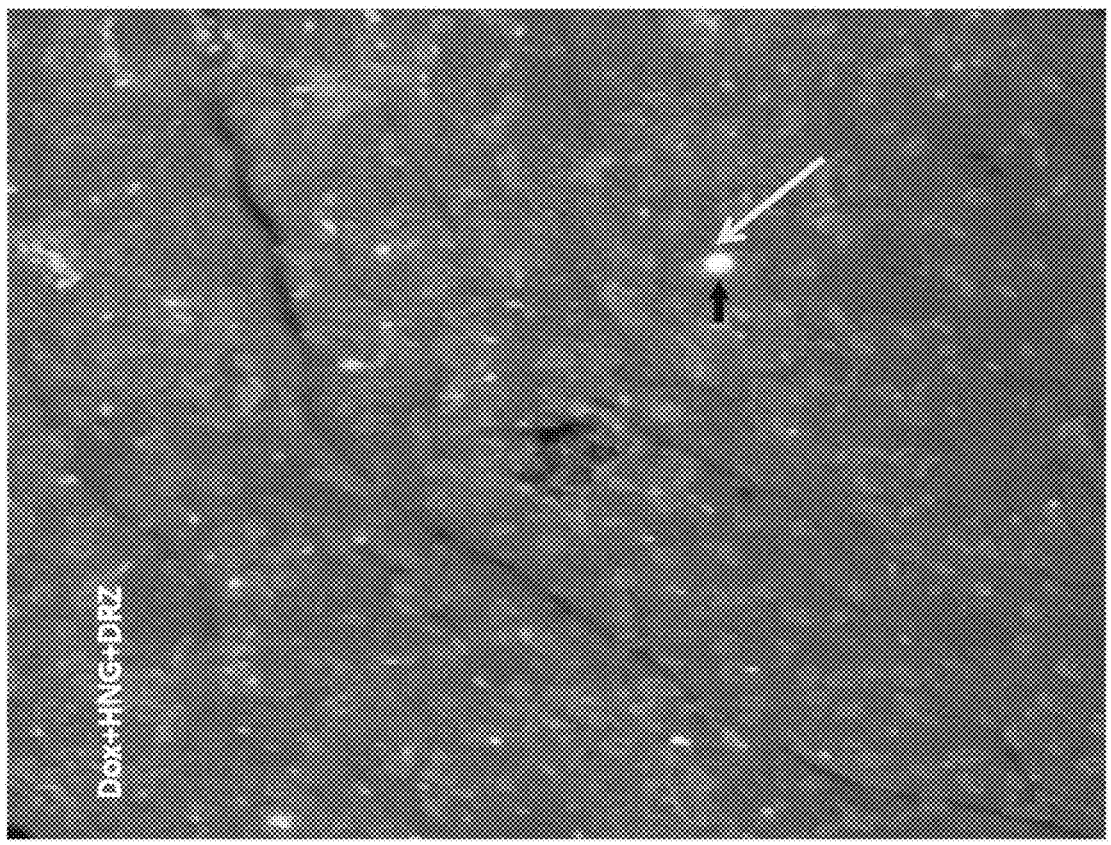
Figure 11C:
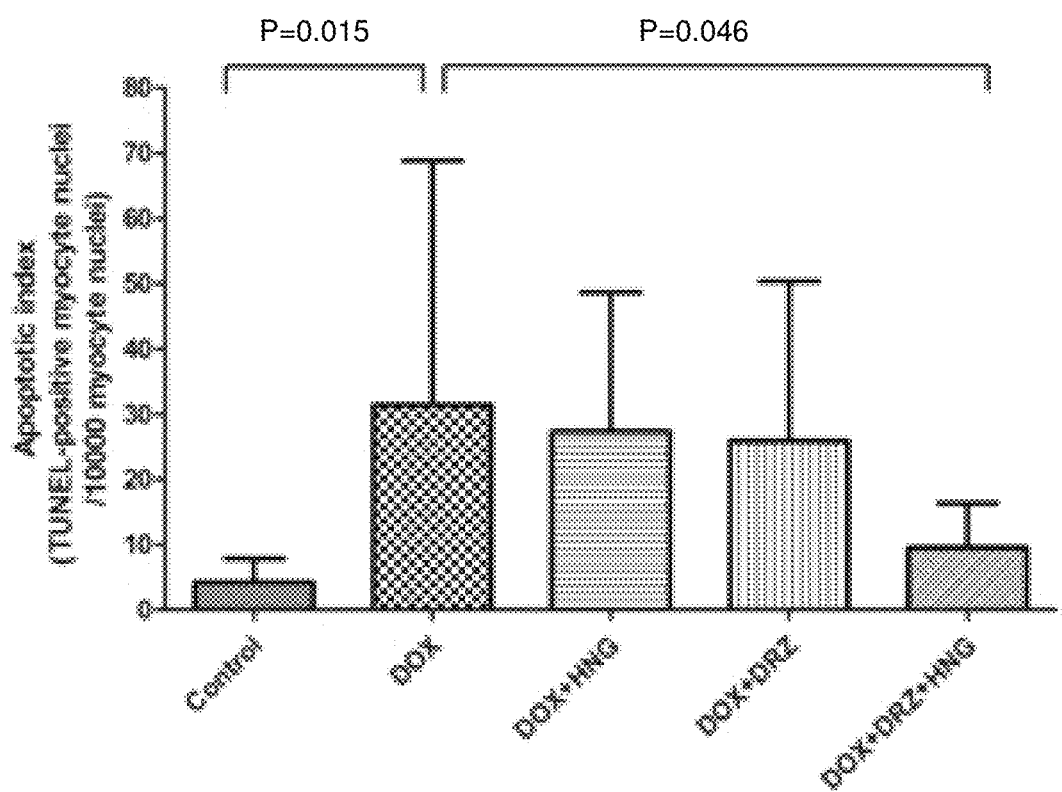

DRZ, HNG or DRZ+HNG only treatment did not induce significant levels of cardiomyocytes apoptosis at basal state. Dox treatment alone significantly increased cardiomyocytes apoptosis. While there was no markedly protective effect of DRZ treatment on reduction of Dox-induced apopotosis at ten weeks after treatment, combined treatment of DRZ+HNG significantly reduced the Dox-induced cardiomyocytes apoptosis to control levels (FIG. 11).

Dox-Induced Cardiac Fibrosis

Figures 12A, 12B, 12C:
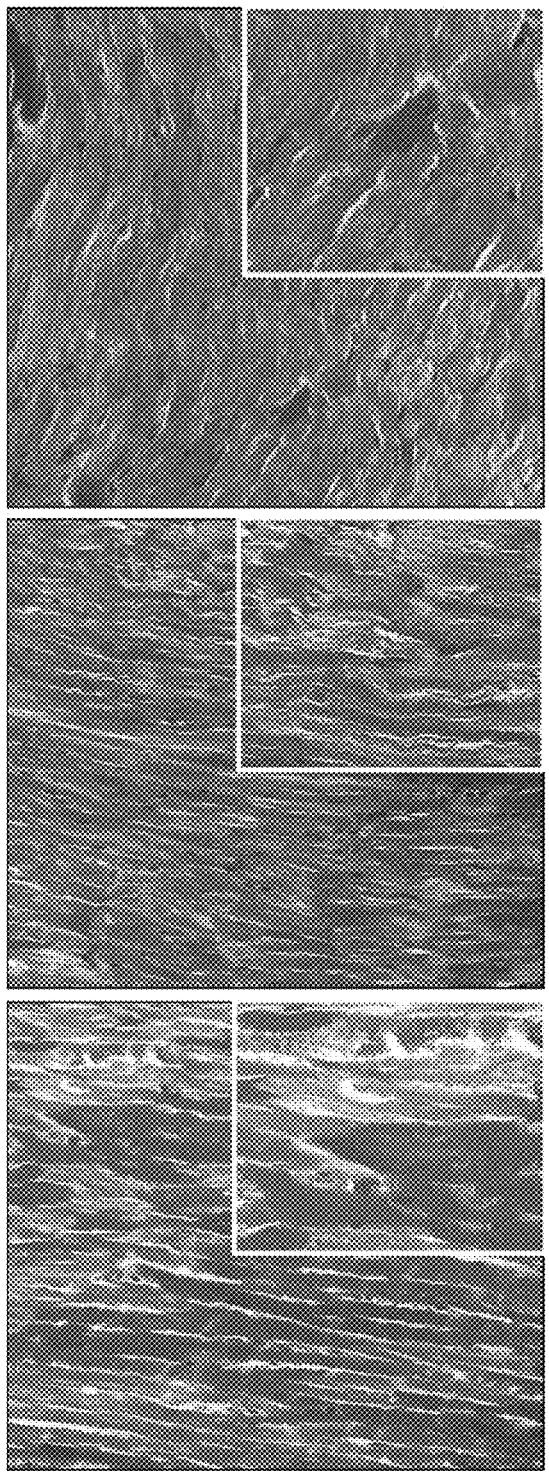
FIGS. 12A-C show representative Masson Trichrome Staining for fibrosis in FIG. 12A control, FIG. 12B Dox only treated, and FIG. 12C Dox+HNG+DRZ treated mouse hearts.
Figure 12D:
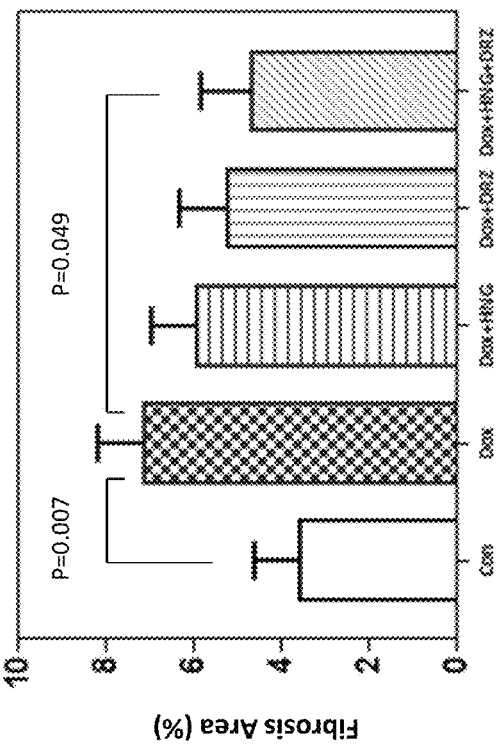
FIG. 12D shows cardiac fibrosis response in control (Saline (Sal)), HNG, DRZ, DRZ+HNG, Dox, Dox+HNG, Dox+DRZ and Dox+DRZ+HNG treated mice as indicated on the x-axis. HNG+DRZ significantly attenuated Dax-induced cardiac fibrosis response.
Figure 17B:
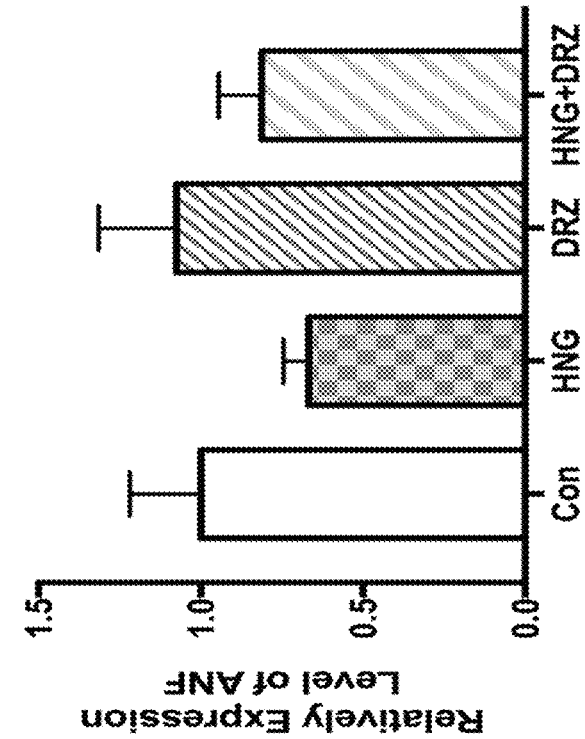
FIG. 17B shows quantitative assessment of fibrosis area of heart sections stained by Masson Trichrome in control, HNG, DRZ, and HNG+DRZ treated mice.

While there were no changes of fibrosis in hearts treated with HNG, DRZ, or HNG+DRZ (FIG. 17B), Dox only treatment significantly induced a cardiac fibrosis response as compared to controls. Although HNG or DRZ treatment did not reduce Dox-induced cardiac fibrosis in Dox-treated mice, the combined treatment of HNG and DRZ significantly decreased Dox-induced cardiac fibrosis to near control levels (FIG. 12).

Cardiac Mitochondria Related Gene Expression

Figure 13:
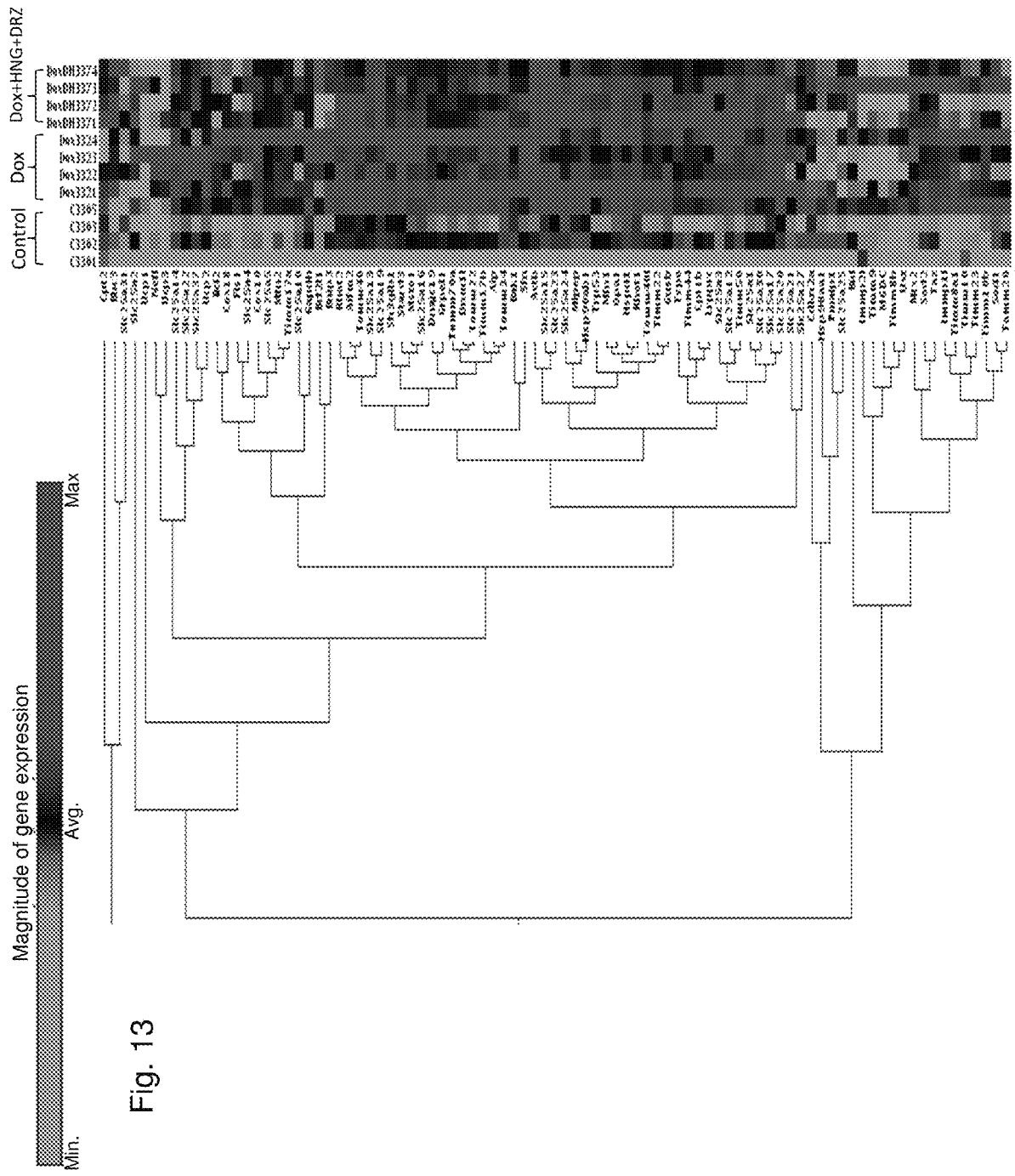
FIG. 13 shows a heat map indicating co-regulated genes across groups of control, Dox alone, and Dox+HNG+DRZ treated mice. Using a threshold of 1.1 fold, among the 84 gene examined, Dox only treatment induced up-regulation of 78 genes and down-regulation of 5 genes as compared to control. In contrast, as compared to Dox treatment alone, HNG+DRZ+Dox resulted in down-regulation of 40 genes toward control levels, and up-regulation of 11 genes. Red or near red color indicates indicate up-regulation, and green and near green color indicates down-regulation.
Figure 14A:
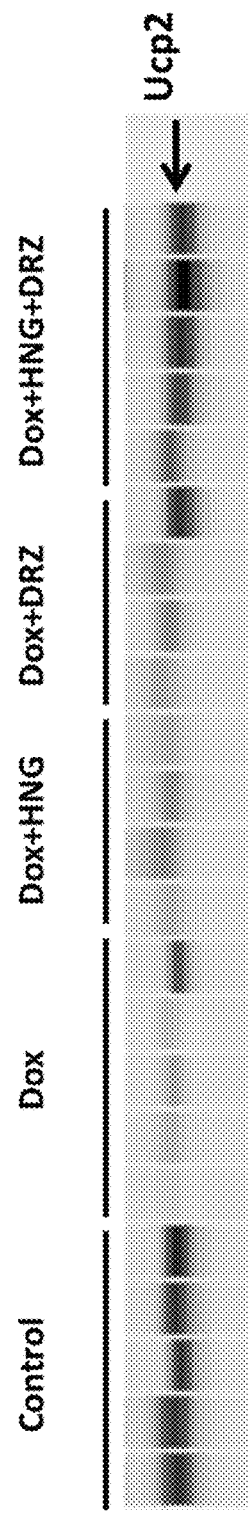
FIGS. 14A-B show Ucp2 protein levels assessed by Western blot using ProteinSimple assay for control, Dox, Dox+HNG, Dox+DRZ, and Dox+HNG+DRZ treated mice.
Figure 14B:
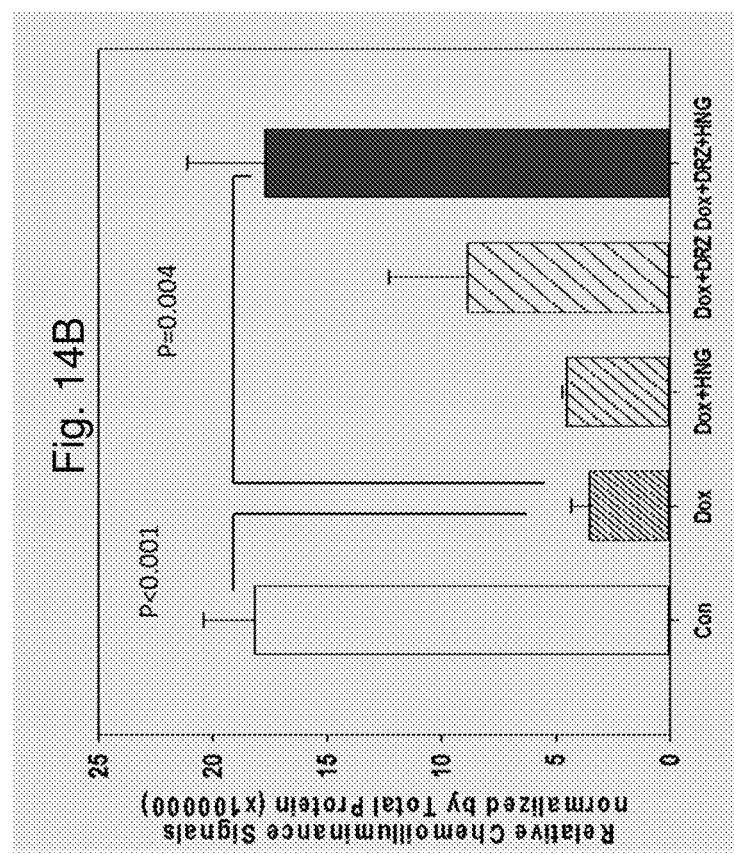

The involvement of the mitochondria in the induction of Dox-induced cardiac dysfunction was explored to seek mechanisms by which the combined HNG and DRZ treatment was effective in preventing Dox-induced cardiomyopathy. The effects of Dox or Dox+HNG+DRZ on nuclear-gene-encoded mitochondrial-gene expression to saline-treated control mice were compared. Among the 84 genes examined, Dox induced up-regulation of 78 genes, and down-regulation of 5 genes as compared to control (threshold of 1.1 fold, FIG. 13). Using a threshold of 2-fold, Dox was found to induce upregulation of 12 genes including Ucp2 and Ucp3 as compared to control (Table 7). When compared with Dox only treatment, combined treatment (HNG+DRZ+Dox) resulted in down-regulation of 40 genes in the direction of the untreated controls, including Ucp2 and Ucp3. The data from qRT-PCR showed that Dox treatment increased Ucp2 and Ucp3 mRNA expression, and HNG, DRZ or combined treatment reversed Dox-induced Ucp2 and Ucp3 mRNA expression to control levels. Mitochondrial Ucp2 protein levels were assessed by a protein-immunoassay. Inconsistent with mRNA expression, we found that Dox alone significantly decreased Ucp2 protein expression as compared to control. Combined HNG+DRZ significantly restored Dox-induced Ucp2 expression to control levels (FIG. 14).

TABLE 7

Fold Changes in Gene Expression after Treatment with DOX alone or with HNG + DRZ

| Gene Symbol | Dox-induced gene expression (Fold changes as compared to control) | Dox + HNG + DRZ induced gene expression (Fold changes as compared to Dox treatment) |
| --- | --- | --- |
| Bbc3 | 3.27 | 1.32 |
| Bcl2 | 2.23 | −1.49 |
| Cox18 | 2.01 | −1.50 |
| Nefl | 3.07 | −2.02 |
| Sfn | 2.55 | −1.45 |
| Slc25a17 | 2.00 | −1.10 |
| Slc25a20 | 2.53 | −1.07 |
| Slc25a21 | 2.35 | −1.19 |
| Slc25a22 | 3.12 | −1.27 |
| Slc25a23 | 5.83 | 1.07 |
| Ucp2 | 2.03 | −1.46 |
| Ucp3 | 2.73 | −2.13 |

Note:
positive number indicates up-regulation, and negative number indicates down-regulation.

Doxorubicin (Dox) causes dose-dependent cumulative adverse effects on cardiac function in man limiting its effectiveness in cancer chemotherapy. Using a mouse model, Dox-induced cardiac dysfunction (decreased heart rate, left ventricle posterior wall thickening, fractional shortening, and ejection fraction) did not occur until 8 weeks after Dox treatment with an accumulative dose of 24 mg/kg body weight in mice. Dox treatment increased cardiomyocyte apoptosis and cardiac fibrosis. These cumulative effects of Dox-induced cardiac dysfunction in mice mimicked the cardiac dysfunction in cancer patients treated with Dox.

Using this Dox-induced cardiotoxicity mouse model, HNG, a synthetic humanin analogue, alone or in combination with DRZ, was evaluated to determine if HNG, alone or in combination with DRZ, could prevent or ameliorate Dox-induced cardiac dysfunction and cardiomyopathy in mice. Moderate cytoprotective effect of HNG treatment alone on Dox-induced cardiac dysfunction was observed. DRZ improved heart function impaired by Dox treatment. However, combined HNG and DRZ treatment resulted in greater protection against Dox-induced cardiac dysfunction than either HNG or DRZ treatment alone. The protective effect of HNG+DRZ against Dox-induced cardiotoxicity was associated with maintenance of body weight to the levels similar to control mice, and all ten mice were healthy and alive at the end of study. Thus, HNG in combination with DRZ prevented Dox-induced cardiac dysfunction and general toxicity.

Data herein showed that the combined treatment of HNG+DRZ significantly decreased Dox-induced apoptosis and intracardiac fibrosis. Without being limited to theory, the addition of HNG to DRZ might strengthen anti-ROS function of DRZ and attenuate the Dox-induced mitochondrial damage resulting in greater cardiac protection. The results from the targeted analysis for mitochondrial related gene expression provided evidence showing that Dox treatment resulted in a global disturbance of mitochondrial gene expression, affecting 78 out of 84 measured genes as compared to control, and HNG+DRZ treatment ameliorated mitochondrial gene changes by reducing 40 out of 84 genes that were elevated by Dox treatment. These results suggested that combined HNG+DRZ treatment blunted the Dox-induced mitochondrial disturbance in the heart as a possible mechanism of the observed cardiac protection.

The data herein shows that HNG+DRZ administration reversed a Dox-induced reduction of Ucp2 protein levels further suggesting that combined HNG and DZR treatment protected mitochondria from Dox-induced damage. In contrast to the protein changes observed, the gene microarray data herein showed that Ucp2 mRNA was upregulated by Dox and reduced by HNG+DRZ co-treatment. The discrepancy between mRNA and protein levels was in line with the general notion that mRNA levels were not sufficient to predict the corresponding protein levels, and post-translational mechanism may have a significant contribution to the overall mitochondrial remodeling. Despite this discrepancy, HNG+DRZ reversed the Dox-induced decrease in Ucp2 protein levels or increased Ucp2 mRNA levels to control levels. Ucp2 protein is a member of mitochondrial transport proteins that regulated the mitochondrial membrane potential created by the proton gradient across the inner mitochondrial membrane. Increased Ucp2 induces proton conductance, and the enhanced proton conductance suppresses ROS production. It was determined that Dox treatment decreased Ucp2 protein in the heart. HNG+DRZ treatment prevented Dox-induced reduction of Ucp2 which might lead to suppressed ROS production and reduced DOX-induced cardiotoxicity.

In conclusion, HNG and DRZ provide enhanced cardioprotective effects against Dox-induced cardiomyopathy; and this observed synergistic cardioprotective effects of combined treatment with HNG and DRZ may result from a preservation of mitochondrial function in the heart.

REFERENCES

Bachar A R, Scheffer L, Schroeder A S, Nakamura H K, Cobb L J, Oh Y K, Lerman L O, Pagano R E, Cohen P & Lerman A. (2010) Humanin is expressed in human vascular walls and has a cytoprotective effect against oxidized LDL-induced oxidative stress. *Cardiovasc. Res.* 88, 360-366.

Berthiaume J M & Wallace K B. (2007) Adriamycin-induced oxidative mitochondrial cardiotoxicity. *Cell Biol. Toxicol.* 23, 15-25.

Chiba T, Nishimoto I, Aiso S & Matsuoka M. (2007) Neuroprotection against neurodegenerative diseases: development of a novel hybrid neuroprotective peptide Colivelin. *Mol. Neurobiol.* 35, 55-84.

Colon E, Strand M L, Carlsson-Skwirut C, Wahlgren A, Svechnikov K V, Cohen P & Soder O. (2006) Anti-apoptotic factor humanin is expressed in the testis and prevents cell-death in leydig cells during the first wave of spermatogenesis. *J. Cell. Physiol.* 208, 373-385.

Eriksson E, Wickstrom M, Perup L S, Johnsen J I, Eksborg S, Kogner P & Savendahl L. (2014) Protective role of humanin on bortezomib-induced bone growth impairment in anticancer treatment. *J. Natl. Cancer Inst.* 106, djt459.

Gammella E, Maccarinelli F, Buratti P, Recalcati S & Cairo G. (2014) The role of iron in anthracycline cardiotoxicity. *Frontiers in pharmacology* 5, 25.

Guo S & Wong S. (2014) Cardiovascular toxicities from systemic breast cancer therapy. *Front Oncol* 4, 346.

Hoang P T, Park P, Cobb L J, Paharkova-Vatchkova V, Hakimi M, Cohen P & Lee K W. (2009) The neurosurvival factor Humanin inhibits beta-cell apoptosis via signal transducer and activator of transcription 3 activation and delays and ameliorates diabetes in nonobese diabetic mice. *Metabolism*.

Hoang P T, Park P, Cobb L J, Paharkova-Vatchkova V, Hakimi M, Cohen P & Lee K W. (2010) The neurosurvival factor Humanin inhibits beta-cell apoptosis via signal transducer and activator of transcription 3 activation and delays and ameliorates diabetes in nonobese diabetic mice. *Metabolism.* 59, 343-349.

Jia Y, Lue Y H, Swerdloff R, Lee K W, Cobb L J, Cohen P & Wang C. (2013) The cytoprotective peptide humanin is induced and neutralizes Bax after pro-apoptotic stress in the rat testis. *Andrology* 1, 651-659.

Jung S S & Van Nostrand W E. (2003) Humanin rescues human cerebrovascular smooth muscle cells from Abeta-induced toxicity. *J. Neurochem.* 84, 266-272.

Kariya S, Hirano M, Furiya Y & Ueno S. (2005) Effect of humanin on decreased ATP levels of human lymphocytes harboring A3243G mutant mitochondrial DNA. *Neuropeptides* 39, 97-101.

Kariya S, Takahashi N, Hirano M & Ueno S. (2003) Humanin improves impaired metabolic activity and prolongs survival of serum-deprived human lymphocytes. *Mol. Cell. Biochem.* 254, 83-89.

Kariya S, Takahashi N, Ooba N, Kawahara M, Nakayama H & Ueno S. (2002) Humanin inhibits cell death of serum-deprived PC 12 h cells. *Neuroreport* 13, 903-907.

Lue Y, Swerdloff R, Liu Q, Mehta H, Hikim A S, Lee K W, Jia Y, Hwang D, Cobb L J, Cohen P & Wang C. (2010) Opposing roles of insulin-like growth factor binding protein 3 and humanin in the regulation of testicular germ cell apoptosis. *Endocrinology* 151, 350-357.

Muzumdar R H, Huffman D M, Atzmon G, Buettner C, Cobb L J, Fishman S, Budagov T, Cui L, Einstein F H, Poduval A, Hwang D, Barzilai N & Cohen P. (2009) Humanin: a novel central regulator of peripheral insulin action. *PLoS One* 4, e6334.

Muzumdar R H, Huffman D M, Calvert J W, Jha S, Weinberg Y, Cui L, Nemkal A, Atzmon G, Klein L, Gundewar S, Ji S Y, Lavu M, Predmore B L & Lefer D J. (2010) Acute humanin therapy attenuates myocardial ischemia and reperfusion injury in mice. *Arterioscler. Thromb. Vac. Biol.* 30, 1940-1948.

Niikura T, Sidahmed E, Hirata-Fukae C, Aisen P S & Matsuoka Y. (2011) A humanin derivative reduces amyloid Beta accumulation and ameliorates memory deficit in triple transgenic mice. *PLoS One* 6, e16259.

Nishimoto I, Matsuoka M & Niikura T. (2004) Unravelling the role of Humanin. *Trends Mol Med* 10, 102-105.

Sponne I, Fifre A, Koziel V, Kriem B, Oster T & Pillot T. (2004) Humanin rescues cortical neurons from prion-peptide-induced apoptosis. *Mol. Cell. Neurosci.* 25, 95-102.

Wallace K B. (2003) Doxorubicin-induced cardiac mitochondrionopathy. *Pharmacol. Toxicol.* 93, 105-115.

Wang D, Li H, Yuan H, Zheng M, Bai C, Chen L & Pei X. (2005) Humanin delays apoptosis in K562 cells by down-regulation of P38 MAP kinase. *Apoptosis* 10, 963-971.

Xu X, Chua C C, Gao J, Hamdy R C & Chua B H. (2006) Humanin is a novel neuroprotective agent against stroke. *Stroke* 37, 2613-2619.

Xu X, Chua K W, Chua C C, Liu C F, Hamdy R C & Chua B H. (2010) Synergistic protective effects of humanin and necrostatin-1 on hypoxia and ischemia/reperfusion injury. *Brain Res.* 1355, 189-194.

Yeh E T. (2006) Cardiotoxicity induced by chemotherapy and antibody therapy. *Annu. Rev. Med* 57, 485-498.

Yeh E T, Tong A T, Lenihan D J, Yusuf S W, Swafford J, Champion C, Durand J B, Gibbs H, Zafarmand A A & Ewer M S. (2004) Cardiovascular complications of cancer therapy: diagnosis, pathogenesis, and management. *Circulation* 109, 3122-3131.

Zhang W, Li Z, Hao J, Zhang Z, Liu L, Mao N, Miao J & Zhang L. (2012) S14G-humanin improves cognitive deficits and reduces amyloid pathology in the middle-aged APPswe/PS1dE9 mice. *Pharmacol. Biochem. Behav.* 100, 361-369.

Zhang X, Urbieta-Caceres V H, Eirin A, Bell C C, Crane J A, Tang H, Jordan K L, Oh Y K, Zhu X Y, Korsmo M J, Bachar A R, Cohen P, Lerman A & Lerman L O. (2012) Humanin prevents intra-renal microvascular remodeling and inflammation in hypercholesterolemic ApoE deficient mice. *Life Sci.* 91, 199-206.

Gao C, Ren S, Lee J H, Qiu J, Chapski D J, Rau C D, Zhou Y, Abdellatif M, Nakano A, Vondriska T M, Xiao X, Fu X D, Chen J N and Wang Y. (2016) RBFox1-mediated RNA splicing regulates cardiac hypertrophy and heart failure. *J Clin Invest.* 126:195-206.

Wang J J-C, Rau C, Avetisyan R, Ren S, Romay M C, Stolin G, Gong K W, Wang Y and Lusis A J. (2016) Genetic Dissection of Cardiac Remodeling in an Isoproterenol-Induced Heart Failure Mouse Model. *PLOS Genetics.* 12:e1006038.

Gao C, Howard-Quijano K, Rau C, Takamiya T, Song Y, Shivkumar K, Wang Y and Mahajan A. (2017) Inflammatory and apoptotic remodeling in autonomic nervous system following myocardial infarction. *PLOS ONE.* 12:e0177750.

Sun R, Wang J, Zheng Y, Li X, Xie T, Li R, Liu M, Cao Y, Lu L, Zhang Q and Zhang P. (2017) Traditional Chinese medicine baoxin decoction improves cardiac fibrosis of rats with dilated cardiomyopathy. *Experimental and Therapeutic Medicine.* 13:1900-1906.

Zhang Y, et al. (2015) Potent Paracrine Effects of human induced Pluripotent Stem Cell-derived Mesenchymal Stem Cells Attenuate Doxorubicin-induced Cardiomyopathy. *Sci Rep.* 5:11235.

Yu W, Sun H, Zha W, Cui W, Xu L, Min Q and Wu J. (2017) Apigenin Attenuates Adriamycin-Induced Cardiomyocyte Apoptosis via the PI3K/AKT/mTOR Pathway. *Evidence-Based Complementary and Alternative Medicine.* vol. 2017:2590676.

Hohensinner P J, Takacs N, Kaun C, Thaler B, Krychtiuk K A, Pfaffenberger S, Aliabadi A, Zuckermann A, Huber K and Wojta J. (2017) Urokinase plasminogen activator protects cardiac myocytes from oxidative damage and apoptosis via hOGG1 induction. *Apoptosis.* 22:1048-1055.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications can be made to the foregoing without departing from the basic aspects of the technology. Although the technology has been described in substantial detail with reference to one or more specific embodiments, those of ordinary skill in the art will recognize that changes can be made to the embodiments specifically disclosed in this application, yet these modifications and improvements are within the scope and spirit of the technology.

The technology illustratively described herein suitably can be practiced in the absence of any element(s) not specifically disclosed herein. Thus, for example, in each instance herein any of the terms "comprising," "consisting essentially of," and "consisting of" can be replaced with either of the other two terms. The terms and expressions which have been employed are used as terms of description and not of limitation, and use of such terms and expressions do not exclude any equivalents of the features shown and described or segments thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed can be resorted to by those skilled in the art, and such modifications and variations are considered within the scope of this technology.

Certain embodiments of the technology are set forth in the claim(s) that follow(s).

What is claimed is:

1. A method of reducing, decreasing, or inhibiting cardiotoxicity caused or induced by a cardiotoxic anti-cancer or anti-tumor therapeutic agent, comprising administering to a subject prior to, during or after treatment with the cardiotoxic anti-cancer or anti-tumor therapeutic agent an amount of:
   (a) a humanin analog comprising the sequence of SEQ ID NO: 2; and
   (b) Dexrazoxane or a salt thereof sufficient to reduce, decrease, or inhibit cardiotoxicity in the subject.

2. A method of protecting or preserving cardiac function in a subject administered a cardiotoxic anti-cancer or anti-tumor therapeutic agent, wherein cardiac function is reduced, decreased, or inhibited by the cardiotoxic anti-cancer or anti-tumor therapeutic agent, comprising administering to the subject prior to, during or after administration of the cardiotoxic anti-cancer or anti-tumor therapeutic agent an amount of:
   (a) a humanin analog comprising the sequence of SEQ ID NO: 2; and
   (b) Dexrazoxane or a salt thereof sufficient to protect or preserve cardiac function in the subject.

3. The method of claim 1, wherein the subject has a hyperproliferative disease or disorder.

4. The method of claim 1, wherein the subject has a metastatic or non-metastatic neoplasia, tumor, cancer or malignancy.

5. The method of claim 1, wherein the cardiotoxic anti-cancer or anti-tumor therapeutic agent comprises an alkylating agent, an anthracycline, an anti-metabolite, plant extract, plant alkaloid, nitrosourea, hormone, nucleoside or nucleotide analog.

6. The method of claim 1, wherein the cardiotoxic anti-cancer or anti-tumor therapeutic agent comprises a DNA intercalating agent or an agent that attaches or bonds to DNA.

7. The method of claim 1, wherein the cardiotoxic anti-cancer or anti-tumor therapeutic agent comprises Doxorubicin, Epirubicin, Idarubicin, Daunorubicin, Valrubicin, Mitoxantrone, Paclitaxel, Cisplatin, Carboplatin, Oxiplatin, Trastuzumab, Bevacizumab, Lapatinib, Alemtuzumab or Imatinib.

8. The method of claim 1, wherein the cardiotoxic anti-cancer or anti-tumor therapeutic agent is not Daunorubicin.

9. The method of claim 1, wherein the method or use reduces, decreases, or inhibits damage to cardiac cells or cardiac tissue.

10. The method of claim 1, wherein the method or use reduces, decreases, or inhibits cardiac mortality.

11. The method of claim 1, wherein the method or use reduces, decreases, or inhibits impairment of cardiac function as determined by electrocardiogram, magnetic resonance imaging (MRI) or computerized tomography (CT) scan.

12. The method of claim 1, wherein the method or use reduces, decreases, or inhibits impairment of cardiac function caused or induced by the cardiotoxic anti-cancer or anti-tumor therapeutic agent.

13. The method of claim 12, wherein the cardiac function impairment comprises a decrease in ejection fraction and/or fractional ventricular shortening.

14. The method of claim 1, wherein the method or use restores, stabilizes, inhibits or prevents a reduction or decrease in ejection fraction and/or fractional ventricular shortening caused or induced by the anti-cancer or anti-tumor therapeutic agent.

15. The method of claim 1, wherein the humanin analog does not substantially reduce, decrease, suppress or inhibit efficacy or activity of the cardiotoxic anti-cancer or anti-tumor therapeutic agent.

16. The method of claim 15, wherein the efficacy or activity of the cardiotoxic anti-cancer or anti-tumor therapeutic agent comprises partial or complete destruction of a hyperproliferating cell, or a neoplastic, tumor, cancer or malignant cell mass, volume, size or numbers of cells; stimulating, inducing or increasing hyperproliferating cell or neoplastic, tumor, cancer or malignant cell necrosis, lysis or apoptosis; reduces hyperproliferating cell or neoplasia, tumor, cancer or malignancy volume size or cell mass; inhibits or prevents progression or an increase in hyperproliferating cell or neoplasia, tumor, cancer or malignancy volume, mass, size or cell numbers, reduces neoplasia, tumor, cancer or malignancy metastasis volume, size or cell mass; or prolongs lifespan.

17. The method of claim 4, wherein the neoplasia, tumor, cancer or malignancy is metastatic, non-metastatic or benign.

18. The method of claim 4, wherein the neoplasia, tumor, cancer or malignancy comprises a solid cellular mass.

19. The method of claim 4, wherein the neoplasia, tumor, cancer or malignancy comprises hematopoietic cells.

20. The method of claim 4, wherein the neoplasia, tumor, cancer or malignancy comprises a carcinoma, sarcoma, lymphoma, leukemia, adenoma, adenocarcinoma, melanoma, glioma, glioblastoma, meningioma, neuroblastoma, retinoblastoma, astrocytoma, oligodendrocytoma, mesothelioma, reticuloendothelial, lymphatic or haematopoietic neoplasia, tumor, cancer or malignancy.

21. The method of claim 20, wherein the sarcoma comprises a lymphosarcoma, liposarcoma, osteosarcoma, chondrosarcoma, leiomyosarcoma, rhabdomyosarcoma or fibrosarcoma.

22. The method of claim 20, wherein the haematopoietic cell neoplasia, tumor, cancer or malignancy comprises a myeloma, lymphoma or leukemia.

23. The method of claim 4, wherein the neoplasia, tumor, cancer or malignancy comprises a metastatic melanoma.

24. The method of claim 4, wherein the neoplasia, tumor, cancer or malignancy comprises a lung, thyroid, head or neck, nasopharynx, throat, nose or sinuses, brain, spine, breast, adrenal gland, pituitary gland, thyroid, lymph, gastrointestinal (mouth, esophagus, stomach, duodenum, ileum, jejunum (small intestine), colon, rectum), genito-urinary tract (uterus, ovary, cervix, endometrial, bladder, testicle, penis, prostate), kidney, pancreas, liver, bone, bone marrow, lymph, blood, muscle, or skin, lung, biliary tract, or hematologic neoplasia, tumor, or cancer.

25. The method of claim 1, wherein the humanin analog is administered at least once a week, at least three times a week, at least once a day, at least twice a day or at least three times a day.

26. The method of claim 1, wherein the subject is a human.

\* \* \* \* \*

SEQUENCE LISTING

```
<160> NUMBER OF SEQ ID NOS: 39

<210> SEQ ID NO 1
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide
```

```
<400> SEQUENCE: 1

Met Ala Pro Arg Gly Phe Ser Cys Leu Leu Leu Leu Thr Ser Glu Ile
1               5                   10                  15

Asp Leu Pro Val Lys Arg Arg Ala
            20

<210> SEQ ID NO 2
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 2

Met Ala Pro Arg Gly Phe Ser Cys Leu Leu Leu Leu Thr Gly Glu Ile
1               5                   10                  15

Asp Leu Pro Val Lys Arg Arg Ala
            20

<210> SEQ ID NO 3
<211> LENGTH: 25
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 3

Met Ala Pro Arg Gly Phe Ser Cys Leu Leu Leu Leu Thr Asp Ser Glu
1               5                   10                  15

Ile Asp Leu Pro Val Lys Arg Arg Ala
            20                  25

<210> SEQ ID NO 4
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 4

Met Ala Pro Ala Gly Ala Ser Cys Leu Leu Leu Leu Thr Gly Glu Ile
1               5                   10                  15

Asp Leu Pro Val Lys Arg Arg Ala
            20

<210> SEQ ID NO 5
<211> LENGTH: 25
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 5

Met Ala Pro Ala Gly Ala Ser Cys Leu Leu Leu Leu Thr Asp Ser Glu
1               5                   10                  15

Ile Asp Leu Pro Val Lys Arg Arg Ala
            20                  25
```

```
<210> SEQ ID NO 6
<211> LENGTH: 18
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 6

Pro Ala Gly Ala Ser Cys Leu Leu Leu Leu Thr Asp Ser Glu Ile Asp
1               5                   10                  15

Leu Pro

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 7

Pro Ala Gly Ala Ser Arg Leu Leu Leu Leu Thr Gly Glu Ile Asp Leu
1               5                   10                  15

Pro

<210> SEQ ID NO 8
<211> LENGTH: 32
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 8

Glu Phe Leu Ile Val Ile Lys Ser Met Ala Pro Arg Gly Phe Ser Cys
1               5                   10                  15

Leu Leu Leu Leu Thr Ser Glu Ile Asp Leu Pro Val Lys Arg Arg Ala
            20                  25                  30

<210> SEQ ID NO 9
<211> LENGTH: 32
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 9

Glu Phe Leu Ile Val Ile Lys Ser Met Ala Pro Arg Gly Phe Ser Cys
1               5                   10                  15

Leu Leu Leu Leu Thr Gly Glu Ile Asp Leu Pro Val Lys Arg Arg Ala
            20                  25                  30

<210> SEQ ID NO 10
<211> LENGTH: 32
<212> TYPE: PRT
<213> ORGANISM: Artificial Sequence
<220> FEATURE:
<223> OTHER INFORMATION: Description of Artificial Sequence: Humanin
      Polypeptide
```

```
<400> SEQUENCE: 10

Glu Phe Leu Ile Val Ile Lys Ser Met Ala Pro Ala Gly Ala Ser Cys
1               5                   10                  15

Leu Leu Leu Leu Thr Gly Glu Ile Asp Leu Pro Val Lys Arg Arg Ala
            20                  25                  30

<210> SEQ ID NO 11
<211> LENGTH: 26
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 11

Ser Ala Leu Leu Arg Ser Ile Pro Ala Pro Ala Gly Ala Ser Arg Leu
1               5                   10                  15

Leu Leu Leu Thr Gly Glu Ile Asp Leu Pro
            20                  25

<210> SEQ ID NO 12
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 12

Met Ala Pro Arg Gly Phe Ser Cys Arg Leu Leu Leu Thr Ser Glu Ile
1               5                   10                  15

Asp Leu Pro Val Lys Arg Arg Ala
            20

<210> SEQ ID NO 13
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide
<220> FEATURE:
<221> NAME/KEY: misc_feature
<222> LOCATION: (24)..(24)
<223> OTHER INFORMATION: Xaa can be any naturally occurring amino acid

<400> SEQUENCE: 13

Met Thr Pro Arg Gly Phe Ser Cys Leu Leu Leu Pro Thr Ser Glu Thr
1               5                   10                  15

Asp Leu Pro Val Lys Arg Arg Xaa
            20

<210> SEQ ID NO 14
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide
<220> FEATURE:
<221> NAME/KEY: misc_feature
<222> LOCATION: (23)..(24)
<223> OTHER INFORMATION: Xaa can be any naturally occurring amino acid
```

```
<400> SEQUENCE: 14

Met Ala Pro Arg Gly Phe Ser Cys Leu Leu Leu Ser Thr Ser Glu Ile
1               5                   10                  15

Asp Leu Pro Val Lys Arg Xaa Xaa
            20

<210> SEQ ID NO 15
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 15

Met Ala Pro Arg Gly Phe Ser Cys Leu Leu Leu Ser Thr Ser Glu Ile
1               5                   10                  15

Asp Leu Pro Val Lys Arg Arg Ala
            20

<210> SEQ ID NO 16
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 16

Met Cys His Trp Ala Gly Gly Ala Ser Asn Thr Gly Asp Ala Arg Gly
1               5                   10                  15

Asp Val Phe Gly Lys Gln Ala Gly
            20

<210> SEQ ID NO 17
<211> LENGTH: 26
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 17

Met Gly Val Lys Phe Phe Thr Leu Ser Thr Arg Phe Phe Pro Ser Val
1               5                   10                  15

Gln Arg Ala Val Pro Leu Trp Thr Asn Ser
            20                  25

<210> SEQ ID NO 18
<211> LENGTH: 38
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 18

Met Leu Gly Tyr Asn Phe Ser Ser Phe Pro Cys Gly Thr Ile Ser Ile
1               5                   10                  15

Ala Pro Gly Phe Asn Phe Tyr Arg Leu Tyr Phe Ile Trp Val Asn Gly
            20                  25                  30

Leu Ala Lys Val Val Trp
            35
```

```
<210> SEQ ID NO 19
<211> LENGTH: 26
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 19

Met Leu Glu Val Met Phe Leu Val Asn Arg Arg Gly Lys Ile Cys Arg
1               5                   10                  15

Val Pro Phe Thr Phe Phe Asn Leu Ser Leu
            20                  25

<210> SEQ ID NO 20
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 20

Met Tyr Cys Ser Glu Val Gly Phe Cys Ser Glu Val Ala Pro Thr Glu
1               5                   10                  15

Ile Phe Asn Ala Gly Leu Val Val
            20

<210> SEQ ID NO 21
<211> LENGTH: 20
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 21

Met Leu Asp Gln Asp Ile Pro Met Val Gln Pro Leu Leu Lys Val Arg
1               5                   10                  15

Leu Phe Asn Asp
            20

<210> SEQ ID NO 22
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide
<220> FEATURE:
<221> NAME/KEY: SITE
<222> LOCATION: (14)..(14)
<223> OTHER INFORMATION: Xaa is P - Serine

<400> SEQUENCE: 22

Met Ala Pro Arg Gly Phe Ser Cys Leu Leu Leu Leu Thr Xaa Glu Ile
1               5                   10                  15

Asp Leu Pro Val Lys Arg Arg Ala
            20

<210> SEQ ID NO 23
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide
```

```
<220> FEATURE:
<221> NAME/KEY: SITE
<222> LOCATION: (7)..(7)
<223> OTHER INFORMATION: Xaa is P - Serine

<400> SEQUENCE: 23

Met Ala Pro Arg Gly Phe Xaa Cys Leu Leu Leu Leu Thr Ser Glu Ile
1               5                   10                  15

Asp Leu Pro Val Lys Arg Arg Ala
            20

<210> SEQ ID NO 24
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide
<220> FEATURE:
<221> NAME/KEY: SITE
<222> LOCATION: (7)..(7)
<223> OTHER INFORMATION: Xaa is P - Serine
<220> FEATURE:
<221> NAME/KEY: SITE
<222> LOCATION: (14)..(14)
<223> OTHER INFORMATION: Xaa is P - Serine

<400> SEQUENCE: 24

Met Ala Pro Arg Gly Phe Xaa Cys Leu Leu Leu Leu Thr Xaa Glu Ile
1               5                   10                  15

Asp Leu Pro Val Lys Arg Arg Ala
            20

<210> SEQ ID NO 25
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide
<220> FEATURE:
<221> NAME/KEY: SITE
<222> LOCATION: (14)..(14)
<223> OTHER INFORMATION: Xaa is D - Serine

<400> SEQUENCE: 25

Met Ala Pro Arg Gly Phe Ser Cys Leu Leu Leu Leu Thr Xaa Glu Ile
1               5                   10                  15

Asp Leu Pro Val Lys Arg Arg Ala
            20

<210> SEQ ID NO 26
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide
<220> FEATURE:
<221> NAME/KEY: SITE
<222> LOCATION: (7)..(7)
<223> OTHER INFORMATION: Xaa is D - Serine

<400> SEQUENCE: 26

Met Ala Pro Arg Gly Phe Xaa Cys Leu Leu Leu Leu Thr Ser Glu Ile
1               5                   10                  15

Asp Leu Pro Val Lys Arg Arg Ala
            20
```

```
<210> SEQ ID NO 27
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide
<220> FEATURE:
<221> NAME/KEY: SITE
<222> LOCATION: (7)..(7)
<223> OTHER INFORMATION: Xaa is D - Serine
<220> FEATURE:
<221> NAME/KEY: SITE
<222> LOCATION: (14)..(14)
<223> OTHER INFORMATION: Xaa is D - Serine

<400> SEQUENCE: 27

Met Ala Pro Arg Gly Phe Xaa Cys Leu Leu Leu Leu Thr Xaa Glu Ile
1               5                   10                  15

Asp Leu Pro Val Lys Arg Arg Ala
            20

<210> SEQ ID NO 28
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide
<220> FEATURE:
<221> NAME/KEY: SITE
<222> LOCATION: (14)..(14)
<223> OTHER INFORMATION: Xaa is D - Serine

<400> SEQUENCE: 28

Met Ala Pro Ala Gly Ala Ser Cys Leu Leu Leu Leu Thr Xaa Glu Ile
1               5                   10                  15

Asp Leu Pro Val Lys Arg Arg Ala
            20

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Humanin
      Polypeptide
<220> FEATURE:
<221> NAME/KEY: SITE
<222> LOCATION: (12)..(12)
<223> OTHER INFORMATION: Xaa is D - Serine

<400> SEQUENCE: 29

Pro Ala Gly Ala Ser Cys Leu Leu Leu Leu Thr Xaa Glu Ile Asp Leu
1               5                   10                  15

Pro

<210> SEQ ID NO 30
<211> LENGTH: 32
<212> TYPE: PRT
<213> ORGANISM: Artificial Sequence
<220> FEATURE:
<223> OTHER INFORMATION: Description of Artificial Sequence: Humanin
      Polypeptide
```

<400> SEQUENCE: 30

Glu Phe Leu Ile Val Ile Lys Ser Met Ala Pro Arg Gly Phe Ala Cys
1               5                   10                  15

Leu Leu Leu Leu Thr Ser Glu Ile Asp Leu Pro Val Lys Arg Arg Ala
            20                  25                  30

<210> SEQ ID NO 31
<211> LENGTH: 32
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 31

Glu Phe Leu Ile Val Ile Lys Ser Met Ala Pro Arg Gly Phe Ser Cys
1               5                   10                  15

Leu Leu Leu Leu Thr Gly Glu Ile Asp Leu Pro Val Lys Lys Lys Lys
            20                  25                  30

<210> SEQ ID NO 32
<211> LENGTH: 32
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 32

Glu Phe Leu Ile Val Ile Lys Ser Met Ala Pro Arg Gly Phe Ser Ala
1               5                   10                  15

Leu Leu Leu Leu Thr Ser Glu Ile Asp Leu Pro Val Lys Arg Arg Ala
            20                  25                  30

<210> SEQ ID NO 33
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 33

Met Ala Pro Arg Gly Phe Ser Ala Leu Leu Leu Leu Thr Ser Glu Ile
1               5                   10                  15

Asp Leu Pro Val Lys Arg Arg Ala
            20

<210> SEQ ID NO 34
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide
<220> FEATURE:
<221> NAME/KEY: SITE
<222> LOCATION: (7)..(7)
<223> OTHER INFORMATION: Xaa is D - Serine
<220> FEATURE:
<221> NAME/KEY: SITE
<222> LOCATION: (14)..(14)
<223> OTHER INFORMATION: Xaa is D - Serine

<400> SEQUENCE: 34

Met Ala Pro Arg Gly Phe Xaa Cys Leu Leu Leu Thr Xaa Glu Ile
1               5                   10                  15

Asp Pro Pro Val Lys Arg Arg Ala
                20

<210> SEQ ID NO 35
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 35

Met Ala Pro Arg Gly Phe Ala Cys Leu Leu Leu Thr Ser Glu Ile
1               5                   10                  15

Asp Leu Pro Val Lys Arg Arg Ala
                20

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 36

Pro Arg Gly Phe Ala Cys Leu Leu Leu Thr Ser Glu Ile Asp Leu
1               5                   10                  15

Pro

<210> SEQ ID NO 37
<211> LENGTH: 25
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 37

Tyr Met Ala Pro Arg Gly Phe Ser Cys Leu Leu Leu Thr Gly Glu
1               5                   10                  15

Ile Asp Leu Pro Val Lys Lys Lys Lys
                20                  25

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 38

Glu Phe Leu Ile Val Ile Lys Ser
1               5

<210> SEQ ID NO 39
<211> LENGTH: 17
<212> TYPE: PRT
<213> ORGANISM: Artificial Sequence -continued

```
<220> FEATURE:
<223> OTHER INFORMATION: Description of Artificial Sequence: Humanin
      Polypeptide

<400> SEQUENCE: 39

Pro Arg Gly Phe Ser Cys Leu Leu Leu Leu Thr Gly Glu Ile Asp Leu
1               5                   10                  15

Pro
```